(12) United States Patent
Kaduchak et al.

(10) Patent No.: US 10,545,085 B2
(45) Date of Patent: *Jan. 28, 2020

(54) APPARATUSES, SYSTEMS AND METHODS FOR IMAGING FLOW CYTOMETRY

(71) Applicant: Life Technologies Corporation, Carlsbad, CA (US)

(72) Inventors: Gregory Kaduchak, Chandler, AZ (US); Michael Ward, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/444,232

(22) Filed: Jun. 18, 2019

(65) Prior Publication Data

US 2019/0301997 A1 Oct. 3, 2019

Related U.S. Application Data

(63) Continuation of application No. 15/941,791, filed on Mar. 30, 2018.
(Continued)

(51) Int. Cl.
*G01N 21/00* (2006.01)
*G01N 15/14* (2006.01)
(Continued)

(52) U.S. Cl.
CPC .... *G01N 15/1436* (2013.01); *B01L 3/502761* (2013.01); *G01J 3/4406* (2013.01); *G01N 15/0227* (2013.01); *G01N 15/0272* (2013.01); *G01N 15/1404* (2013.01); *G01N 15/147* (2013.01); *G01N 15/1429* (2013.01); *G01N 15/1434* (2013.01); *G01N 15/1456* (2013.01); *G01N 15/1459* (2013.01); *G01N 15/1468* (2013.01); *G01N 21/532* (2013.01); *G01N 21/6456* (2013.01); *B01L 2200/0652* (2013.01); *B01L 2400/082* (2013.01); *G01N 2015/0003* (2013.01); *G01N 2015/0011* (2013.01); *G01N 2015/03* (2013.01); *G01N 2015/1006* (2013.01); *G01N 2015/1081* (2013.01);
(Continued)

(58) Field of Classification Search
CPC ............... G01N 21/9501; G01N 21/94; G01N 21/8806; G01N 21/956; G01N 21/95607
USPC ...................................................... 356/337
See application file for complete search history.

(56) References Cited

U.S. PATENT DOCUMENTS

| 4,171,159 A | 10/1979 | White |
| 4,193,088 A | 3/1980 | Moran |
(Continued)

FOREIGN PATENT DOCUMENTS

| DE | 10320956 A1 | 8/2004 |
| WO | 2008122051 A1 | 10/2008 |
(Continued)

OTHER PUBLICATIONS

PCT/US2018/025538, "International Search Report mailed", dated Jun. 13, 2018, 4 Pages.

*Primary Examiner* — Md M Rahman
(74) *Attorney, Agent, or Firm* — BakerHostetler

(57) ABSTRACT

The present disclosure provides apparatuses, systems, and methods for performing particle analysis through flow cytometry at comparatively high event rates and for gathering high resolution images of particles.

18 Claims, 20 Drawing Sheets

Related U.S. Application Data

(60) Provisional application No. 62/479,734, filed on Mar. 31, 2017.

(51) Int. Cl.
    *G01N 21/53*    (2006.01)
    *G01N 15/02*    (2006.01)
    *B01L 3/00*    (2006.01)
    *G01N 21/64*    (2006.01)
    *G01J 3/44*    (2006.01)
    *G01N 15/10*    (2006.01)
    *G01N 15/00*    (2006.01)

(52) U.S. Cl.
CPC . *G01N 2015/142* (2013.01); *G01N 2015/149* (2013.01); *G01N 2015/1415* (2013.01); *G01N 2015/1422* (2013.01); *G01N 2015/1438* (2013.01); *G01N 2015/1445* (2013.01); *G01N 2015/1452* (2013.01)

(56) References Cited

U.S. PATENT DOCUMENTS

| | | |
|---|---|---|
| 4,195,221 A | 3/1980 | Moran |
| 4,786,165 A | 11/1988 | Yamamoto et al. |
| 5,159,397 A | 10/1992 | Kosaka et al. |
| 5,159,398 A | 10/1992 | Maekawa et al. |
| 5,247,340 A | 9/1993 | Ogino |
| 5,272,354 A | 12/1993 | Kosaka |
| 5,412,466 A | 5/1995 | Ogino |
| 5,418,371 A | 5/1995 | Aslund et al. |
| 5,426,499 A | 6/1995 | Kosaka et al. |
| 5,428,441 A | 6/1995 | Ogino et al. |
| 5,436,717 A | 7/1995 | Ogino |
| 5,444,527 A | 8/1995 | Kosaka |
| 5,457,526 A | 10/1995 | Kosaka |
| 5,469,251 A | 11/1995 | Kosaka et al. |
| 5,471,294 A | 11/1995 | Ogino |
| 5,594,544 A | 1/1997 | Horiuchi et al. |
| 5,694,216 A | 12/1997 | Riza |
| 5,824,269 A | 10/1998 | Kosaka et al. |
| 6,211,955 B1 | 4/2001 | Basiji et al. |
| 6,256,096 B1 | 7/2001 | Johnson |
| 6,309,886 B1 | 10/2001 | Ambrose et al. |
| 6,381,023 B1 | 4/2002 | Kempe |
| 6,467,350 B1 | 10/2002 | Kaduchak et al. |
| 6,507,391 B2 | 1/2003 | Riley et al. |
| 6,522,781 B1 | 2/2003 | Norikane et al. |
| 6,563,583 B2 | 5/2003 | Ortyn et al. |
| 6,608,680 B2 | 8/2003 | Basiji et al. |
| 6,618,140 B2 | 9/2003 | Frost et al. |
| 6,644,118 B2 | 11/2003 | Kaduchak et al. |
| 6,671,044 B2 | 12/2003 | Ortyn et al. |
| 6,763,149 B2 | 7/2004 | Riley et al. |
| 6,778,263 B2 | 8/2004 | Ortyn et al. |
| 6,813,017 B1 | 11/2004 | Hoffman et al. |
| 6,831,781 B2 | 12/2004 | Tearney et al. |
| 6,875,973 B2 | 4/2005 | Ortyn et al. |
| 6,934,408 B2 | 8/2005 | Frost et al. |
| 6,947,128 B2 | 9/2005 | Basiji et al. |
| 7,009,651 B2 | 3/2006 | Ortyn et al. |
| 7,057,732 B2 | 6/2006 | Jorgenson et al. |
| 7,074,622 B2 | 7/2006 | Qiao et al. |
| 7,161,665 B2 | 1/2007 | Johnson |
| 7,190,832 B2 | 3/2007 | Frost et al. |
| 7,307,721 B2 | 12/2007 | King |
| 7,340,957 B2 | 3/2008 | Kaduchak et al. |
| 7,450,229 B2 | 11/2008 | Ortyn et al. |
| 7,460,248 B2 | 12/2008 | Kurtz et al. |
| 7,522,758 B2 | 4/2009 | Ortyn et al. |
| 7,610,942 B2 | 11/2009 | Harui et al. |
| 7,796,256 B2 | 9/2010 | Sieracki et al. |
| 7,804,594 B2 | 9/2010 | Vacca et al. |
| 7,835,000 B2 | 11/2010 | Graves et al. |
| 7,837,040 B2 | 11/2010 | Ward et al. |
| 8,005,314 B2 | 8/2011 | Ortyn et al. |
| 8,054,542 B2 | 11/2011 | Sasaki et al. |
| 8,083,068 B2 | 12/2011 | Kaduchak et al. |
| 8,103,080 B2 | 1/2012 | George et al. |
| 8,131,053 B2 | 3/2012 | Ortyn et al. |
| 8,134,705 B2 | 3/2012 | Kaduchak et al. |
| 8,150,136 B2 | 4/2012 | George et al. |
| 8,174,704 B2 | 5/2012 | Kim |
| 8,199,331 B2 | 6/2012 | Rembe et al. |
| 8,227,257 B2 | 7/2012 | Ward et al. |
| 8,263,407 B2 | 9/2012 | Goddard et al. |
| 8,266,950 B2 | 9/2012 | Kaduchak et al. |
| 8,266,951 B2 | 9/2012 | Kaduchak et al. |
| 8,309,408 B2 | 11/2012 | Ward et al. |
| 8,436,993 B2 | 5/2013 | Kaduchak et al. |
| 8,440,952 B2 | 5/2013 | Jalali et al. |
| 8,451,524 B2 | 5/2013 | Ortyn et al. |
| 8,507,293 B2 | 8/2013 | Ward et al. |
| 8,528,406 B2 | 9/2013 | Goddard et al. |
| 8,564,776 B2 | 10/2013 | Graves et al. |
| 8,610,085 B2 | 12/2013 | Patt |
| 8,654,441 B2 | 2/2014 | Jalali et al. |
| 8,675,196 B2 | 3/2014 | Ozasa |
| 8,714,014 B2 | 5/2014 | Kaduchak et al. |
| 8,736,818 B2 | 5/2014 | Weimer et al. |
| 8,761,486 B2 | 6/2014 | Heng et al. |
| 8,767,208 B2 | 7/2014 | Graves et al. |
| 8,783,109 B2 | 7/2014 | Kaduchak et al. |
| 8,817,115 B1 | 8/2014 | Venkatachalam |
| 8,846,408 B2 | 9/2014 | Ward et al. |
| 8,863,958 B2 | 10/2014 | Kaduchak et al. |
| 8,865,476 B2 | 10/2014 | Ward et al. |
| 8,873,051 B2 | 10/2014 | Kaduchak et al. |
| 8,879,797 B2 | 11/2014 | Sieracki et al. |
| 8,900,870 B2 | 12/2014 | Ward et al. |
| 8,932,520 B2 | 1/2015 | Goddard et al. |
| 9,013,692 B2 | 4/2015 | Hu et al. |
| 9,023,294 B2 | 5/2015 | Terazono et al. |
| 9,038,467 B2 | 5/2015 | Kaduchak et al. |
| 9,068,916 B2 | 6/2015 | Heng |
| 9,074,979 B2 | 7/2015 | Kaduchak et al. |
| 9,097,889 B2 | 8/2015 | Kalkbrenner et al. |
| 9,134,271 B2 | 9/2015 | Ward et al. |
| 9,201,008 B2 | 12/2015 | Theriault et al. |
| 9,217,635 B2 | 12/2015 | Guetta |
| 9,279,750 B2 | 3/2016 | Cremins et al. |
| 9,316,635 B2 | 4/2016 | Farrell et al. |
| 9,339,744 B2 | 5/2016 | Kaduchak et al. |
| 9,372,143 B2 | 6/2016 | Yamamoto et al. |
| 9,423,353 B2 | 8/2016 | Diebold et al. |
| 9,457,139 B2 | 10/2016 | Ward et al. |
| 9,476,855 B2 | 10/2016 | Ward et al. |
| 9,488,621 B2 | 11/2016 | Kaduchak et al. |
| 9,494,509 B2 | 11/2016 | Graves et al. |
| 9,529,008 B2 | 12/2016 | Smith et al. |
| 9,704,019 B2 | 7/2017 | Suzuki et al. |
| 9,726,593 B2 | 8/2017 | Kaduchak et al. |
| 9,733,171 B2 | 8/2017 | Ward et al. |
| 9,909,117 B2 | 3/2018 | Kaduchak et al. |
| 10,001,434 B2 | 6/2018 | Kaduchak et al. |
| 2001/0006416 A1 | 7/2001 | Johnson |
| 2002/0148738 A1* | 10/2002 | Boyd ................... G01N 33/32 205/782 |
| 2003/0137666 A1 | 7/2003 | Johnson |
| 2005/0112541 A1* | 5/2005 | Durack ................ C12N 5/0612 435/2 |
| 2005/0115313 A1* | 6/2005 | Luchsinger ........... G01F 1/6986 73/204.18 |
| 2006/0139638 A1* | 6/2006 | Muller .................. G01N 15/12 356/342 |
| 2008/0283401 A1 | 11/2008 | Peach |
| 2009/0148937 A1* | 6/2009 | Schnelle ........... B01L 3/502753 435/325 |
| 2011/0134426 A1 | 6/2011 | Kaduchak et al. |
| 2012/0002029 A1 | 1/2012 | Sieracki et al. |
| 2012/0097099 A1* | 4/2012 | Roeckle ............. B65G 49/0459 118/423 |
| 2014/0147860 A1 | 5/2014 | Kaduchak et al. |

(56) References Cited

U.S. PATENT DOCUMENTS

2014/0261757 A1* 9/2014 Katsumoto ............... F17D 1/00
                                                     137/268
2014/0353522 A1   12/2014 Wu et al.
2016/0244828 A1    8/2016 Mason
2016/0327779 A1* 11/2016 Hillman ............... G02B 21/367
2017/0191922 A1    7/2017 Ward et al.

FOREIGN PATENT DOCUMENTS

| WO | WO-2008122051 A1 * | 10/2008 | ......... G01N 15/1404 |
| WO | 2013132344 A2 | 9/2013 | |
| WO | 2013191772 A1 | 12/2013 | |

* cited by examiner

APPARATUSES, SYSTEMS AND METHODS FOR IMAGING FLOW CYTOMETRY

CROSS REFERENCE TO RELATED APPLICATIONS

The present application is a continuation of now-allowed U.S. patent application Ser. No. 15/941,791, "Apparatuses, Systems and Methods for Imaging Flow Cytometry" (filed Mar. 30, 2018), which claims priority to and the benefit of U.S. Provisional Patent Application No. 62/479,734, "Apparatuses, Systems and Methods for Imaging Flow Cytometry" (filed Mar. 31, 2017). The entireties of all foregoing applications are incorporated herein by reference for any and all purposes.

TECHNICAL FIELD

The present disclosure relates to the field of imaging apparatuses, systems and methods for cells and other particulates in fluid flows.

BACKGROUND

Flow cytometry is the analysis of particles at high speeds, in which cells or particles are transported past a highly focused laser beam where the integrated fluorescence and scattered light are collected by a bank of detectors. It is common for this to be done in a highly parallel fashion where the particle traverses multiple lasers/detection banks during its travel through the system. The resultant data is used to determine the presence or absence of properties such as surface proteins, internal markers, rough estimates of particle shape, and the like. In typical cytometers, this analysis is conducted at rates of 100's to 100,000's of cells per second.

It is desired to collect light associated with as many cells as possible, but in operation, one must avoid a condition termed coincidence. Coincidence occurs when more than one cell/particle is in the laser beam simultaneously. The rate of coincidence is directly proportional to the time a particle spends in the laser (interrogation time). As a general rule, the shorter the interrogation time, the lower the probability of coincidence. For this reason, very low duty cycle (<10%) and short interrogation times on the order of several microseconds are typically employed in an effort to minimize coincidence events.

Interrogation times on the order of microseconds, however, create difficulties in collecting sufficient photons for detection. To overcome this issue, a combination of high power lasers, photoelectron multiplying detectors (such as photomultiplier tubes (PMTs) and avalanche photodiodes (APDs)), and fast electronics are employed. This has been the standard in flow cytometry design for decades. These ultra-short interrogation times are generally acceptable when the signal is the integrated response generated by the entire cell, as is done in traditional flow cytometry approaches. Such short times are, however, problematic if higher spatial resolution data is required, such as imaging the cells in a manner that allows visualization of the cell membrane, nucleus, cytoplasm, and/or organelles.

Due to the short interrogation time required for high analysis rates, high resolution imaging in flow cytometry has been limited. As opposed to collecting the integrated signal from the entire cell, an imaging detector such as a camera must detect light from much smaller locations on the cell on a pixel by pixel basis. The challenge of collecting high resolution images of single cells at high speeds is difficult because the photon count generated by each pixel is much lower than the integrated photon count. For this reason, imaging that is conducted in flow cytometers is generally done with much larger interrogation times to increase photon counts. The larger interrogation times, however, greatly reduce the event rate and therefore imaging flow cytometry is largely utilized in niche applications. Accordingly, there is a long-felt need in the art for apparatuses, systems and methods for imaging flow cytometry that are capable of operating so as to collect information at both comparatively slow and comparatively fast interrogation times.

SUMMARY

In one aspect, the present disclosure provides systems, comprising: a flow channel, the flow channel having an inlet, and the flow channel defining a flow path for fluid communicated therethrough; a first optical train comprising a first illumination source and a first detection module, the first detection module being disposed so as to receive a signal related to illumination of a first region of the flow channel by the first illumination source, the first region being located at a first distance from the inlet of the flow channel; a second optical train comprising a second illumination source and a second detection module, the second detection module being disposed so as to receive a signal related to illumination of a second region of the flow channel by the second illumination source, the second region being located at a second distance from the inlet of the flow channel, the second distance being greater from the first distance, and (a) wherein the first region of the flow channel defines a first cross-sectional area, wherein the second region of the flow channel defines a second cross-sectional area, and wherein the first and second cross-sectional areas differ from one another in area, in shape, or in both area and shape, or (b) wherein (i) the system comprises a conduit entering the flow channel between the inlet of the flow channel and the first region of the flow channel, (ii) the system comprises a conduit entering the flow channel between the first region and the second region of the flow channel, or both (i) and (ii), (c) wherein the system comprises a flowrate modulator configured to modulate a velocity in the flow path, or (d) the system further comprising a field module, the field module being configured to increase or reduce a field at a region of the flow channel so as to move at least some particles in a flow in the flow channel and sensitive to the field from a velocity streamline $S_0$ of particle velocity within the flow in the flow channel to a velocity streamline $S_1$ of particle velocity within the flow in the flow channel, wherein the particle velocity at $S_0$ during system operation differs from the particle velocity at $S_1$, between the first and second regions of the flow channel, or any combination of (a), (b), (c), or (d).

In another aspect, the present disclosure provides methods, comprising: flowing a population of particles through a flow channel; with a first optical train, illuminating at least some of the population of particles at a first region of the flow channel and collecting a first signal related to said illuminating; with a second optical train, illuminating at least some of the population of particles at a second region of the flow channel and collecting a second signal related to said illuminating, a particle velocity at the first region of the flow channel differing from a particle velocity at the second region of the flow channel, and the first signal differing from the second signal.

Further provided are methods, comprising: communicating a population of particles through a flow channel, in a direction from a first region of the flow channel toward a second region of the flow channel; with a first optical train, illuminating at least some of the population of particles at the first region of the flow channel and collecting a first signal related to said illuminating; with a second optical train, illuminating at least some of the population of particles at the second region of the flow channel and collecting a second signal related to said illuminating, increasing or reducing a field on a subset of the particles between the first and second regions of the flow channel, the field being increased or reduced so as to move the subset of particles from a velocity streamline $S_0$ of particle velocity within the flow channel to a velocity streamline $S_1$ of particle velocity within the flow channel, wherein the particle velocity at $S_0$ differs from the particle velocity at $S_1$.

BRIEF DESCRIPTION OF THE DRAWINGS

The summary, as well as the following detailed description, is further understood when read in conjunction with the appended drawings. For the purpose of illustrating the technology, there are shown in the drawings exemplary and preferred embodiments of the invention; however, the disclosure is not limited to the specific methods, compositions, and devices disclosed. In addition, the drawings are not necessarily drawn to scale, and the text labels on the various parts of the drawings are illustrative only and are not limiting of the disclosed technology. In the drawings.

DETAILED DESCRIPTION OF ILLUSTRATIVE EMBODIMENTS

Figure 1:
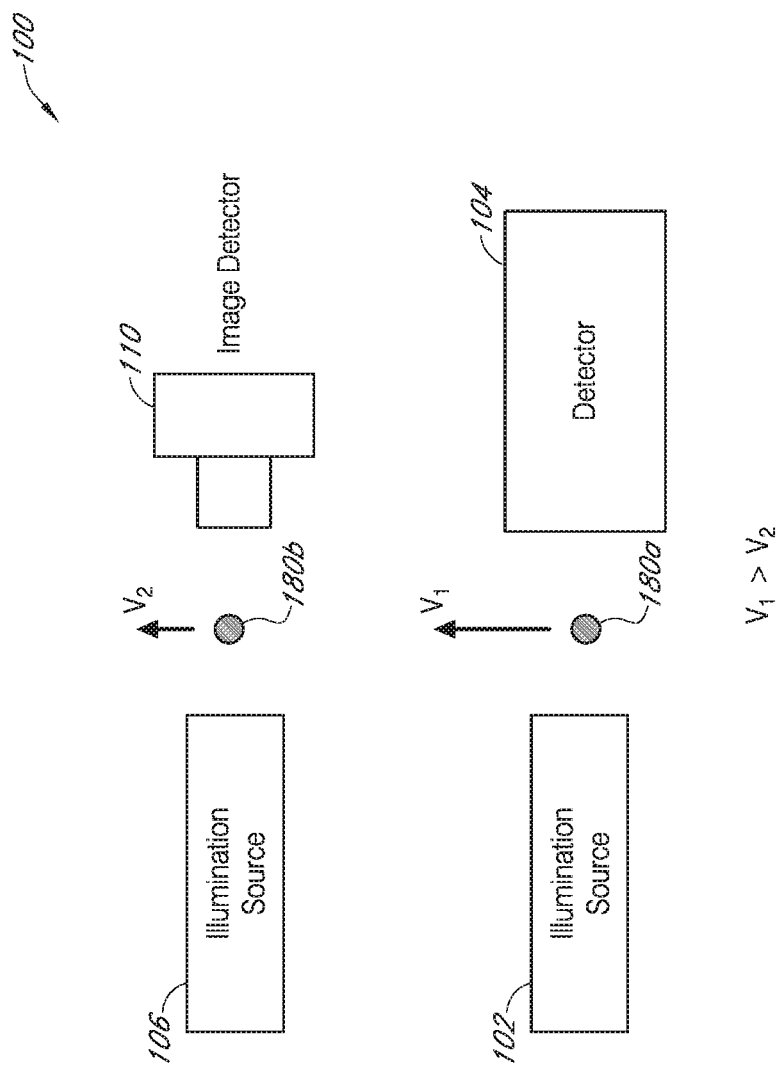
FIG. 1 provides an illustration of a particle traversing different interrogation zones at different velocities.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a", "an", and "the" include plural referents unless the context clearly dictates otherwise. As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps. It is to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

Numerical values in the specification and claims of this application reflect average values. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams (g) to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

Terms

As used herein, "illumination" refers to radiation (visible or not), which may be applied to a particle, cell, or other analyte of interest. It should be understood that the term "illumination" includes the excitation of fluorescent dyes or other moieties, and also includes the application of radiation in the context of bright-field, dark-field, phase-contrast illumination and the like. Similarly, an "illumination source" is a device that performs illumination or one or more components of a device or system that allows illumination to be performed. Lasers, lamps, light-emitting diodes, and the like are considered to be non-limiting examples of illumination sources.

As used herein, "detection" refers to the collection of light, whether reflected, wavelength-shifted, or unreflected, including emitted light (including fluorescence) or light that has interacted with a sample. As one example, a camera that collects visible images performs "detection." Similarly, a "detector" is a device that performs detection or one or more components of a device or system that allows detection to be performed. Photomultiplier tubes (PMTs), silicon photomultipliers (SiPMs), photon counters, avalanche photodiodes (APDs), and the like are considered to be non-limiting examples of detectors.

As used herein, the term "image detector" refers to any type of detector or detection method that allows creation of an image of a particle. Pixelated detectors, slit-scanning optics, frequency multiplexed imaging, time stretch methods, and the like are considered to be an "image detector" capable of producing an image of a particle.

As used herein, the term "traditional flow cytometry data", which is used interchangeably with the term "conventional flow cytometry data", refers to data gathered from light resulting from the interaction of light with particles in a flow stream, e.g., pulse height, area and width. Such traditional flow cytometry data have not historically included imaging data, as traditional flow cytometers have not historically had imaging capabilities. As used herein, the terms "traditional flow cytometer" and "conventional flow cytometer" are used interchangeably.

As explained herein, it is desirable to have an instrument that can collect traditional flow cytometry data at high event rates and low coincidence while also creating high resolution images of the particles. There have been multiple examples of imaging flow cytometry. Most of these prior approaches employed image detectors in a conventional flow cytometer design. However, attempts at imaging particles in flow have resulted in low image capture and analysis rates due to shortfalls in conventional flow cytometer design and available imaging technologies. Presently, there are several technologies addressing higher data rates for imaging flow cytometry. One technology uses time delay integration (TDI) arrays. A TDI array accumulates multiple exposures of a moving object thereby increasing the interrogation time. This technology requires precise knowledge of the particle velocity to allow the detector to track the traversal of the particle. Current systems using this technology have a maximum event rate of only a few thousand particles per second. In addition, conventional flow cytometry data (integrated signal) is processed by finding the cell in the image and integrating within the calculated cell boundary. This processing is memory intensive and time consuming, forcing the data display and analysis to be performed post-data collection.

The second technology is a method that uses frequency multiplexing. In this method, the illumination light is frequency multiplexed into a large array of small pixels. The time domain signature produced by the interaction of the particle with this array of beams is collected by a PMT. An image is then constructed by processing the signal in the frequency domain and assigning pixel locations to specific spectral values. This system operates in a very similar manner to a frequency multiplexing microscope.

Frequency multiplexed imaging has an advantage relative to camera-based systems in a flow cytometer as conventional flow cytometry data (integrated signal) is simpler to acquire. As opposed to analyzing an image, the integrated data is obtained by integrating the time domain signal. But to reduce blur from the moving cell in an image, the particle velocity must be limited to acquire high resolution images. Although the processing of conventional flow cytometry data using this method can be done rapidly, the requirement for lower velocity results in lower data rates than conventional flow cytometers.

Similar to frequency multiplexed imaging, a similar method has been developed to spatially stretch a pulse of light. The illumination comprises a light pulse that has a frequency spectrum extending across the beam. After interacting with the cell, collected light travels through a dispersing element that temporally spreads the pulse of light as a function of frequency. Once the time domain signature is captured, the image is reconstructed by assigning pixels to the amount of light collected as specific times.

In theory, the lower data rates associated with these imaging technologies can be increased by running samples at higher concentrations and lower velocities. This is possible since the increased spatial resolution can be used to better discriminate single cells from one another in the image, thereby reducing the number of coincident events through image processing at the expense of increasing the processing burden and data latency.

In practice, however, increased sample concentration is not always practical or desired. Necessitating higher sample concentrations to achieve data rates of a conventional flow cytometer requires changing sample preparation methods to create samples that are concentrated beyond typical working conditions. The high concentrations also result in more cells sticking to one another, especially for adherent samples.

Compounding the issue of higher concentration samples analyzed at lower velocities is the shallow depth of field associated with the imaging system. Tight positioning of particles in the image plane is required for quality high resolution images due to the limited depth of field required by high magnification optics. Typically, this precise positioning is achieved by utilizing a high ratio of sheath fluid to sample fluid. Thus, to position the particles precisely to accommodate the shallow depth of field, a relatively low volumetric sample input rate is required that further limits event rates.

With the advent of fast, high sensitivity imaging detectors such as electron-multiplying charge-coupled devices (EMC-CDs), intensified charge-coupled devices (ICCDs), complementary metal-oxide-semiconductor (CMOS) devices and the like combined with fast, inexpensive electronics, images of cells passing through an illuminated interrogation zone can be processed at relatively high speeds approaching those of conventional flow cytometers. The present invention describes apparatuses, systems and methods to create and employ a hybrid flow cytometer that can collect integrated particle data at the high event rates of a conventional flow cytometer while also obtaining high resolution images of the particles. A variety of different embodiments are described below.

Multiple Velocity Zones

It is possible to enhance throughput and data quality in a hybrid imaging flow cytometer by creating separate particle interrogation zones within the system by associating a different particle velocity with each zone. FIG. 1 provides one way to create separate particle interrogation zones. As shown in FIG. 1, system 100 may include a first illumination source 102 (in this instance, an illumination source) disposed so as to illuminate a particle at a first position 180a at a location between first illumination source 102 and a detector 104. At the first position 180a, the particle experiences a velocity $V_1$.

The particle then transits to second position 180b, which second position is disposed between a second illumination source 106 and an image detector 110, which is depicted here as a camera. At second position 180b, the particle experiences a velocity $V_2$, where velocity $V_2$ is less than velocity $V_1$. The higher velocity zone ($V_1$) allows for the short interrogation times and low coincidence of a conventional flow cytometer. The lower velocity zone ($V_2$) allows for longer interrogation times that increase integrated photon counts and reduces blur for the imaging device. In addition to the advantages for the imaging method, the resulting image can be processed to resolve coincident events associated with the first position 180a.

Figure 2:
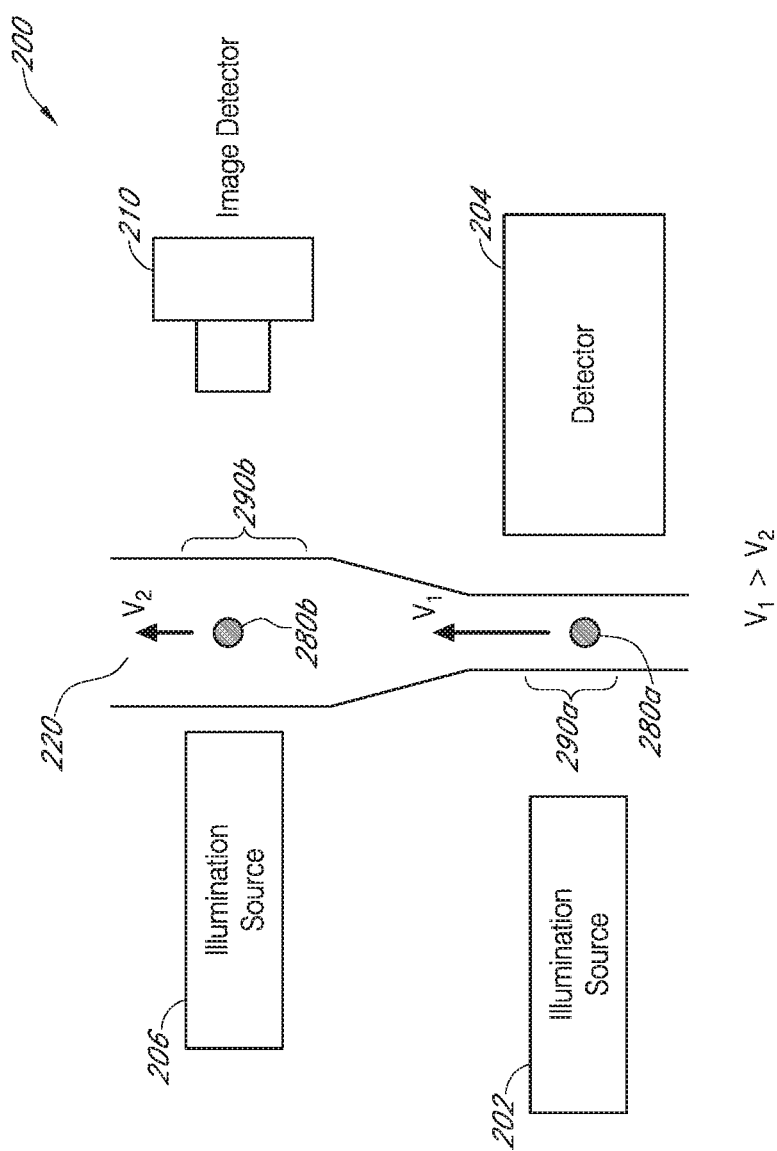
FIG. 2 depicts how a flow cell with differing cross sections can change a particle's velocity between different interrogation locations.

One way to create different velocity zones along the particle path is to change the cross-section of the flow channel. FIG. 2 depicts a system 200 where the cross sectional area of flow channel 220 is changed between two regions. A first region 290a is located between a first illumination source 202 and a detector 204. A second region 290b is located between a second illumination source 206 and an image detector 210. As a particle transits from a first position 280a within the first region 290a to a second position 280b within the second region 290b, the particle experiences a reduction of velocity ($V_1$ at first position 280a and a smaller $V_2$ at second position 280b) on account of the increased cross-sectional area of the flow channel 220 within the second region 290b relative to first region 290a.

As the velocity of the particle can scale proportionally to the cross-sectional area of the flow, a 2× change in the dimension of a square cross-section flow (e.g., a 100 μm×100 μm cross-section changed to a 200 μm×200 μm cross-section) can result in a 4.times. change in the particle velocity. In this example, the total photon count is increased by a factor of four, appreciably raising the signal to noise level of the image detector. In addition, the reduced velocity reduces blur in the image allowing for higher resolution in the dimension parallel to the particle movement.

While the interrogation time is increased, increasing the flow cell dimensions also increases particle position variation. This can increase the requirement for an extended depth of focus, which can degrade image quality. This can be mitigated by expanding the flow cell dimensions by a relatively lesser amount in the direction that is normal to the object plane compared to expansions of the flow cell dimensions in other directions. Alternatively, other mitigation approaches can be employed, such as use of a field focusing technology such as acoustic focusing to better focus particles in the image plane.

An alternative method for changing particle velocity between interrogation zones employs altering the flow characteristics between interrogation zones. Increasing or decreasing the volumetric flow between two interrogation zones can create velocity differences. An example of such a system is shown in FIG. 3A.

Figure 3A:
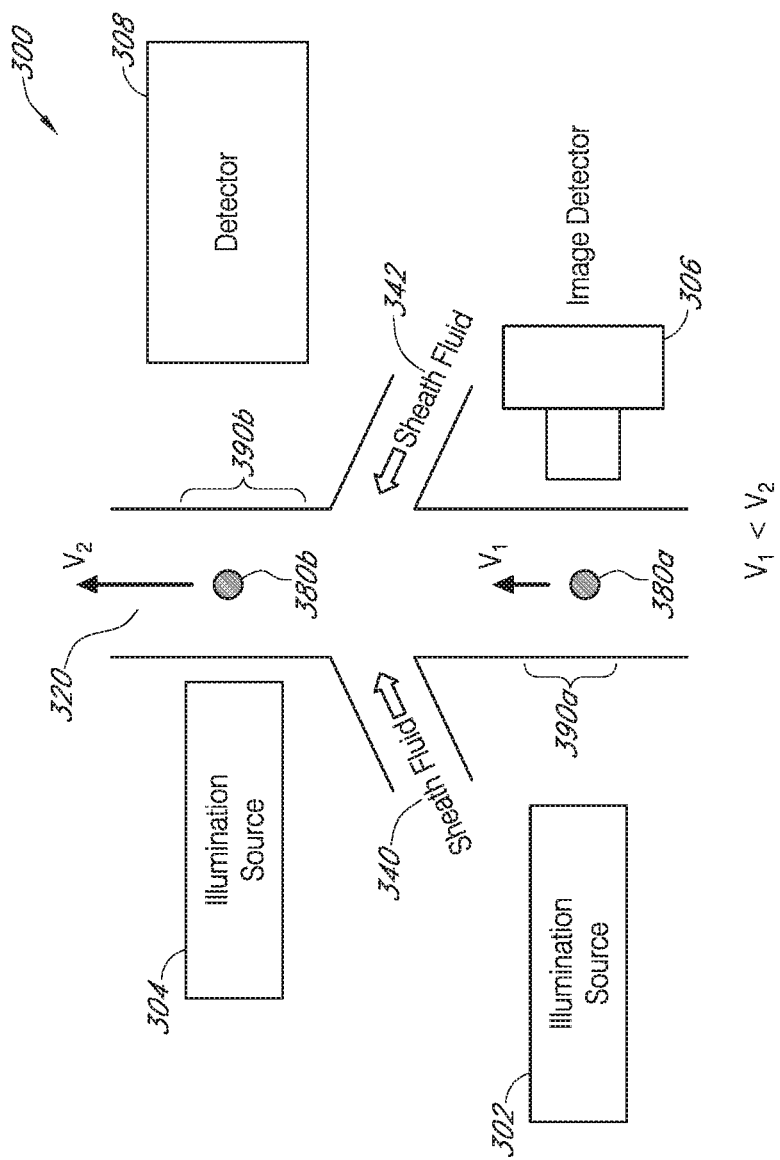
FIG. 3A provides a flow cell that operates by injecting or removing sheath fluid between interrogation zones so as to create a velocity difference for a particle between the interrogation zones.

As shown in FIG. 3A, system 300 includes a flow channel 320, within which a particle transits from a first position 380a within a first region 390a (disposed between a first illumination source 302 and an image detector 306) to a second position 380b within a second region 390b (disposed between a second illumination source 304 and a detector 308). Between the first region 390a and the second region 390b, the flow channel 320 may include a side channel 340 and a side channel 342, which side channels function as conduits to allow for the introduction and/or withdrawal of additional fluid (e.g., sheath fluid) so as to increase or decrease flow velocity between the first position 380a and the second position 380b. As shown in FIG. 3A, the introduction of additional fluid sheath fluid through side channel 340 and side channel 342 provides for the particle having a greater velocity $V_2$ at the second position 380b compared to the earlier lesser velocity $V_1$ at the first position 380a.

In an alternative embodiment, side channel 340 and side channel 342 withdraw fluid from flow channel 320 as opposed to introducing fluid. In such embodiments, the removal of fluid from flow channel 320 between the first position 380a and the second position 380b has the effect of reducing the velocity of the particle such that $V_1$ is greater than $V_2$. For these alternative embodiments, it may be desirable to interchange at least the positions of image detector 306 and detector 308 (i.e., such that image detector 306 obtains an image of the particle at second position 380b). This would provide a benefit to image detector 306 from the increased number of photons that can be collected given the lower velocity $V_2$ in such an embodiment. It may also be desirable to interchange the positions of first illumination source 302 and second illumination source 304 in such embodiments depending on the capabilities and desired output for each.

Furthermore, for embodiments where side channels are used to introduce and/or withdraw fluid from flow channel 320, certain embodiments may utilize only one side channel or conduit between a pair of interrogation zones (e.g., a system 300 with only side channel 340 but not side channel 342). In such embodiments, the effect of employing one side channel will be to move the particle closer to one side wall of flow channel 320. As is known in the art, the velocity of fluid and particles in a flow channel is highest at the center of the channel and decreases as fluid and particles approach the wall of the channel. Such use of a single side channel embodiment can assist in, e.g., slowing the velocity of a particle as the approaches the region of the flow channel subject to an image detector, thus enabling the collection of an increased number of photons as a result of the lower particle velocity near the wall of the channel.

An alternative method for changing the velocity of a particle between interrogation zones employs the use of a flowrate modulator between interrogation zones. An example of such a system is shown in FIG. 3B.

Figure 3B:
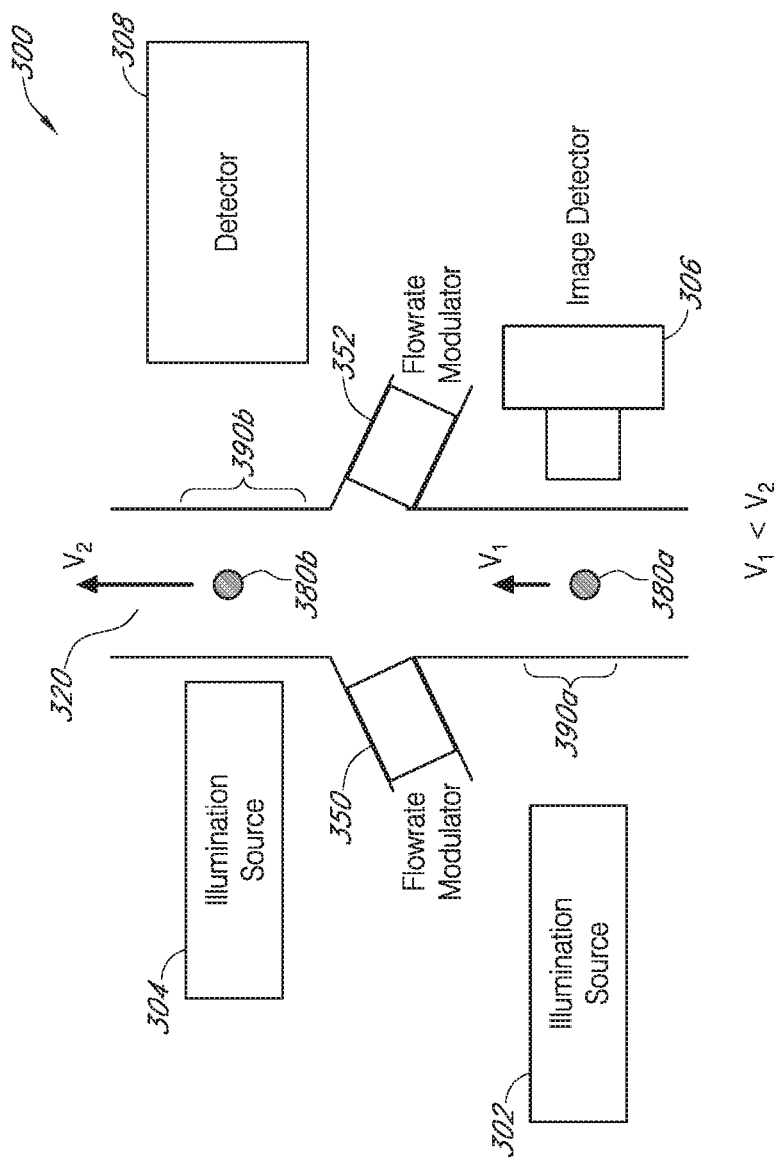
FIG. 3B provides a flow cell that operates by employing a flowrate modulator between interrogation zones so as to create a velocity difference for a particle between the interrogation zones.

As shown in FIG. 3B, system 300 includes a flow channel 320, within which a particle transits from a first position 380a within a first region 390a (disposed between first illumination source 302 and an image detector 306) to a second position 380b within a second region 390b (disposed between a second illumination source 304 and a detector 308). Between the first region 390a and the second region 390b, the system 300 may include flowrate modulator 350 and flowrate modulator 352, which flowrate modulators allow for the increase or decrease of flow velocity between the first position 380a and the second position 380b. Flowrate modulators may comprise, e.g., pumps, valves, and the like. As shown in FIG. 3B, the use of flowrate modulator 350 and flowrate modulator 352 to pump in additional fluid into flow channel 320 provides for the particle having a greater velocity $V_2$ at the second position 380b compared to the earlier lesser velocity $V_1$ at the first position 380a.

In alternative embodiments of FIG. 3B, flowrate modulator 350 and/or flowrate modulator 352 may comprise a valve that, when opened, serves to remove fluid from flow channel 320. Such an embodiment would provide a lesser velocity $V_2$ for the particle at the second position 380b than the earlier higher velocity $V_1$ at first position 380a. Such embodiments may also interchange the positions of image detector 306 and detector 308 if it is desired to position the image detector 306 with the region of flow channel 320 where the particle will have a lesser velocity. As with certain alternative embodiments of FIG. 3A, there are alternative embodiments of FIG. 3B where only a single flowrate modulator is employed. For example, flowrate modulator 350 could be employed as a valve to remove fluid from flow channel 320 when opened, and without any corresponding flowrate modulator 352. In this example, the particle would also move closer to a side wall of flow channel 320, further decreasing its velocity.

An alternative method for changing the velocity of a particle between interrogation zones employs the use of a field module between interrogation zones. An example of such a system is shown in FIG. 3C.

Figure 3C:
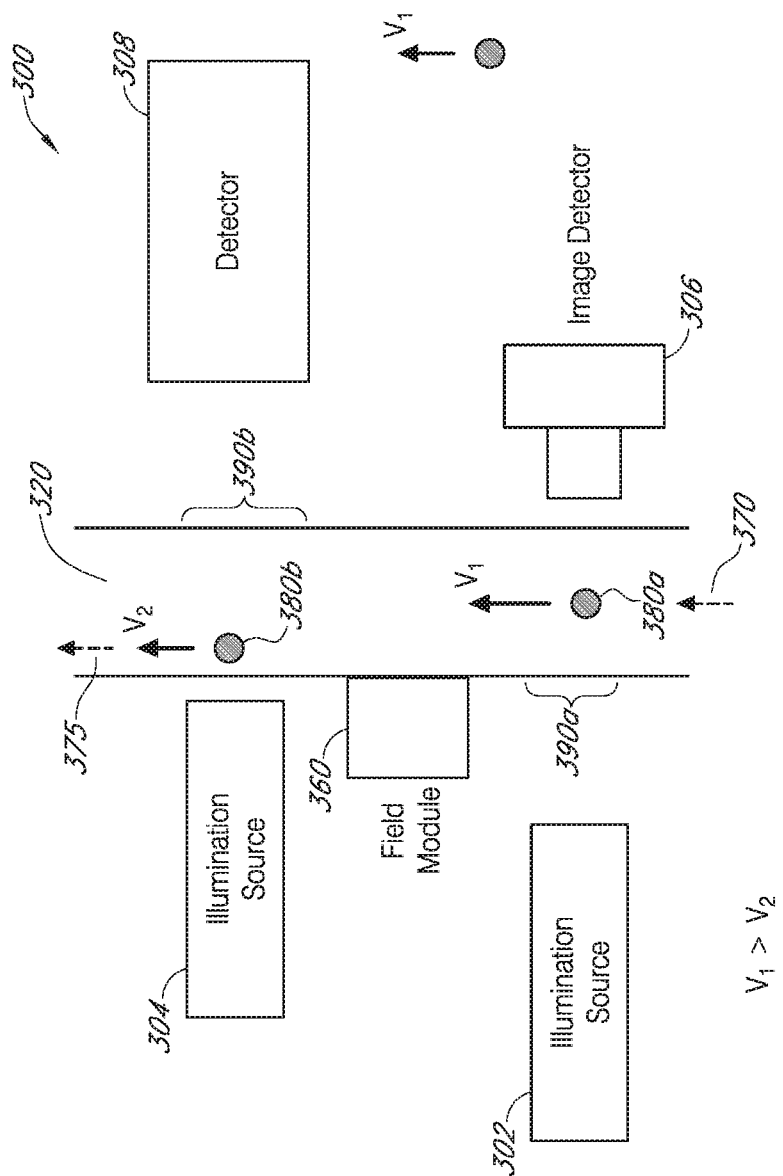
FIG. 3C provides a flow cell that operates by employing a field module between interrogation zones so as to create a velocity difference for a particle between the interrogation zones.

As shown in FIG. 3C, system 300 includes a flow channel 320, within which a particle transits from a first position 380a within a first region 390a (disposed between first illumination source 302 and an image detector 306) to a second position 380b within a second region 390b (disposed between a second illumination source 304 and a detector 308). Between the first region 390a and the second region 390b, the system 300 may include a field module 360, which field module is configured to increase or reduce a field at a region of flow channel 320 in order to reposition particles affected by the field into a different velocity streamline of flow within flow channel 320. (Although only one field module is shown in FIG. 3C, it should be understood that the disclosed technology contemplates the use of both single field modules as well as the use of multiple field modules. As one example, a system according to the present disclosure might include a magnetic field module and also an acoustic field module.) As depicted in FIG. 3C, a particle is within a velocity streamline 370 at first position 380a and is moved into a velocity streamline 375 when the particle is at second position 380b after being moved into velocity streamline 375 by field module 360. This repositioning of the particle has the effect of the velocity $V_2$ of the particle at second position 380b being less than velocity $V_1$ of the particle at first position 380a. Field module 360 may generate a magnetic field, an electric field, an acoustic field, or any combination thereof. If a combination of different fields is employed, system 300 may employ one or more further field modules in addition to field module 360. Thus, one or more field modules may be used such that a given particle experiences different velocities at different regions within a flow chamber.

As can be seen in the above description of various embodiments, just as with slower flow resulting from dimensional changes, slower flow from lower volumetric velocity results in a broader positional distribution of sample particles. This slower flow can similarly be controlled in two dimensions by adding or subtracting more flow in one dimension than another and it can also similarly benefit from field based focusing. If means of differentially controlling the added or subtracted flow are provided, this method can also be used to adjust the particle position in order to achieve better image focus. An advantage for the method of changing the volumetric rate is that each velocity zone can be individually adjusted or dialed in as may be desirable for a particular application. For instance, injecting or removing fluid from a single orifice, thereby repositioning the particle into a lower velocity flow stream, can result in a lower particle velocity. The injection/removal of fluid may be accomplished manually or in an automated fashion. Fluid injection/removal may be constant or change over time.

It should be understood that a system according to the present disclosure may include combining dimensional changes of the flow cell with the increase or decrease of volumetric flow rates. Combining both methods allows designing the flow regions for desired particle velocity, particle distribution, flow channel physical dimensions and overall system configuration (including illumination sources and detectors) with the greatest flexibility.

By selecting the order in which the velocity zones are experienced by a particle, certain advantages can be achieved. For instance, an advantage of having a faster velocity preceding a slower velocity is that the less memory intensive data (e.g., integrated signal from the entire cell) generated in the higher velocity zone can be more readily used to selectively trigger image capture based upon the integrated signal data. By only selectively triggering the image capture device, the amount of data collected and handled is reduced, especially for events that are rare. This feature may, for example, be leveraged to allow increased content images of higher resolution for fewer numbers of cells. This feature may also be used with image technology that benefits from lower duty cycles, such as image intensifiers using multi-channel plates or streak tubes that can become electron depleted when used at very high repetition rates, or image detectors that need a latency period for downloading or processing data. It should be understood that the disclosed technology is well-suited for applications that involve rare events, e.g., events that occur at a frequency of 0.01% and below. The disclosed technology may be used for detection of events at a frequency of 0.01% and below, e.g., from 0.01% to 0.001% or even from 0.01% to 0.00001%.

In some embodiments, a system according to the present disclosure may subject particles to a lower velocity section followed by a high velocity section. Such an embodiment may be useful in situations where one may wish to image a particle at the lower velocity section (e.g., so as improve image resolution) and then increase particle velocity for subsequent sorting and/or conventional flow analysis. By reference to FIG. 1, such an embodiment would be one in which $V_2$ is greater than $V_1$, and wherein the image detector (e.g., a camera or other imager) is present at the $V_1$ upstream location and a detector is present at the downstream $V_2$ location.

It should be understood that embodiments of the disclosed technology may include more than two velocity zones. For example, several sequential velocity changes can be advantageous where cells are interrogated by a host of different detector systems. As one example, a system may include sequential generation of conventional flow data, low resolution image data, and high resolution image data. As another example, a system may include a slow velocity zone for imaging, a comparatively fast velocity zone for conventional flow, and a comparatively still faster velocity zone for better separation during sorting. A system according to the present disclosure may have, e.g., three, four, or even more velocity zones.

Various other embodiments may include changes in orientation of detectors and or illumination sources and or changes in flow direction. For example, FIG. 4 shows a system 400 that includes an image detector 408 with an objective lens configured to capture images along the axis of flow in channel 420.

As shown, a particle may transit from a first position 480a in a first region 490a (disposed between an illumination source 402 and a detector 404) to a second position 480b in second region 490b, where the particle may be subject to illumination from an illumination source 406 and/or from an illumination source 460. As shown in FIG. 4, illumination source 460 is configured to provide epi-illumination. As shown in the figure, the particle experiences a velocity $V_1$ at the first region 490a, which velocity $V_1$ may be greater than the velocity $V_2$ the particle experiences at the second region 490b. Illumination of the particle in second region 490 can optionally be separate from the objective of image detector 408 and/or it can use the objective itself of image detector 408.

Figure 4:
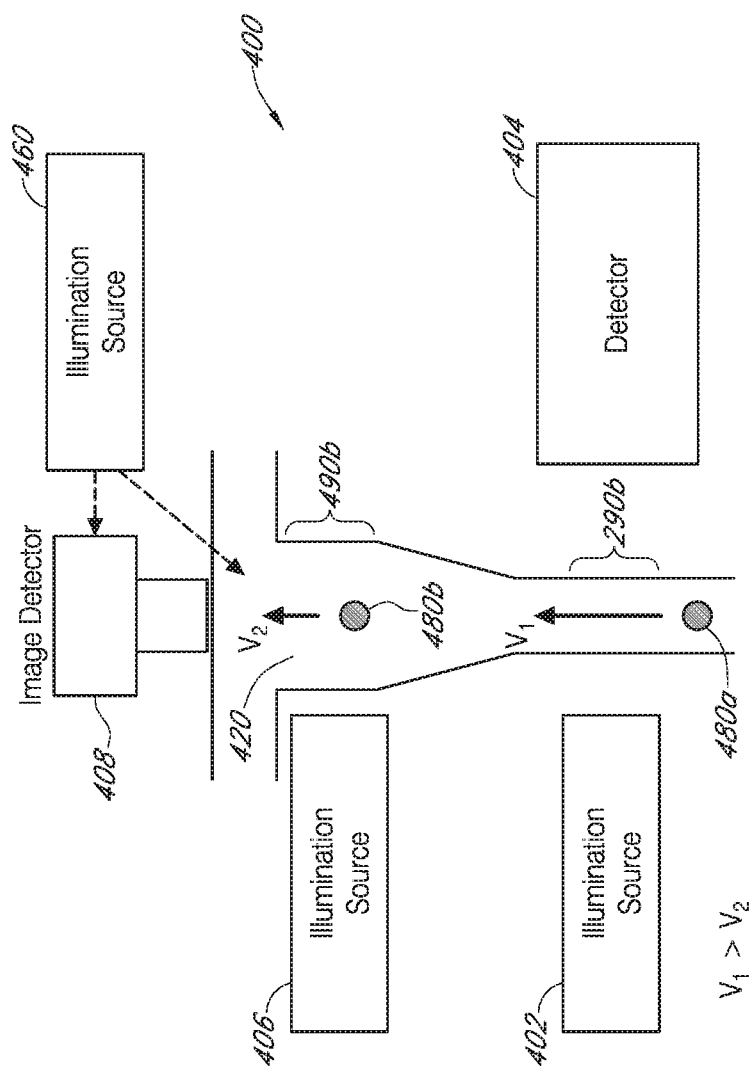
FIG. 4 provides a flow cell that is configured to collect images along the direction of particle flow.
Figure 5:
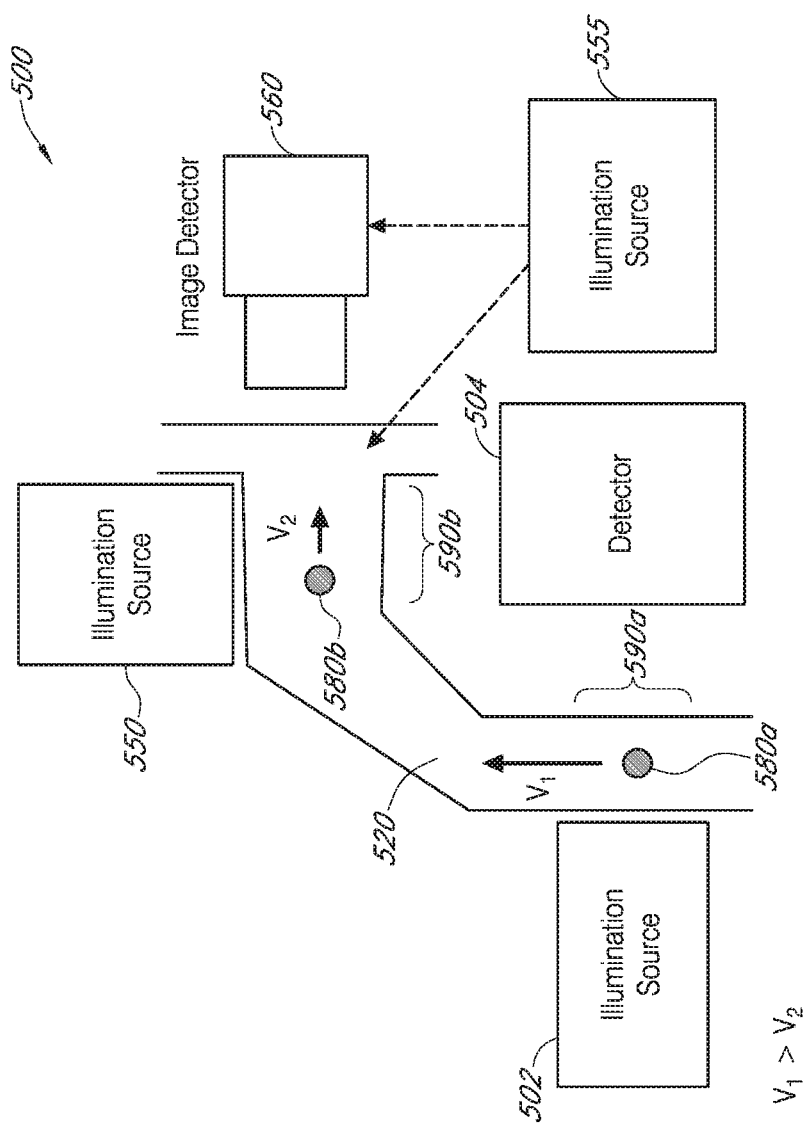
FIG. 5 provides a flow cell configured to collect images along the flow path of a particle; and where the particle's velocity is reduced through an increase in the flow channel dimensions and can be further reduced by proper sizing of the output ports to adjust the particle trajectory.

FIG. 5 provides system 500, the system having an alternative configuration to FIG. 4, with flow within a second region 590b being slower than within a first region 590a. As shown in FIG. 5, a particle may transit within flow channel 520 from a first position 580a to a second position 580b, where the particle has a velocity $V_2$ at the second position 580b that is less than the velocity $V_1$ at first position 580a. As shown, at first position 580a, the particle is disposed between an illumination source 502 and a detector 504. At the second position 580b, the particle may receive illumination from an illumination source 550 and/or an illumination source 555, with corresponding image data collected by image detector 560. As depicted in FIG. 5, illumination source 555 is in an epi configuration. Illumination can optionally be separate from the objective of image detector 560 and/or it can use the objective itself of image detector 560. Geometry changes such as the foregoing may be desirable for physical accommodation of detector or illumination elements, and also for controlling stray light produced by illumination configurations.

In addition, in configurations where the illumination axis is perpendicular or near-perpendicular to the particle movement and the image collection axis is near parallel to the particle movement, stringent depth of field requirements can be greatly reduced as the depth of field is no longer associated with the particle positions in the plane perpendicular to the flow direction, as the particle will flow through the entire region defined by the field depth. In such embodiments, selection of a proper time (as opposed to controlling a lateral position) is all that is required to capture an image in the desired plane.

It should be understood that although the above embodiments have application to flow imaging, the technology has utility for combining standard high speed flow data with any low light level phenomenon that is difficult to detect by conventional methods. For example, single cell chemiluminescence and bioluminescence are difficult to detect at conventional flow speeds. In such alternative embodiments, imaging elements such as image detector 408 within FIG. 4 or image detector 560 within FIG. 5 may not be present, as alternative embodiments may also employ detectors without imaging capabilities as such detectors would also benefit from the increased number of photons that can be collected from these low power signals at slower flow speeds.

Coincidence Gating

In a traditional flow cytometer, data is formed by integrating light scattered/fluorescent light from the entire cell within a detection region. To determine if events are coincident, data is typically plotted for several different parameters that may include pulse height, pulse width, or pulse area. This data is then utilized to determine possible coincidence. This method may serve as an approximation for determining coincident events.

In experiments where coincidence is important, however, improved methods to determine coincidence are needed. The addition of an image generating device or system to a conventional flow cytometer can allow for much improved coincidence detection. An image contains spatial information to determine the presence of more than one cell in the detection region.

Figure 6:
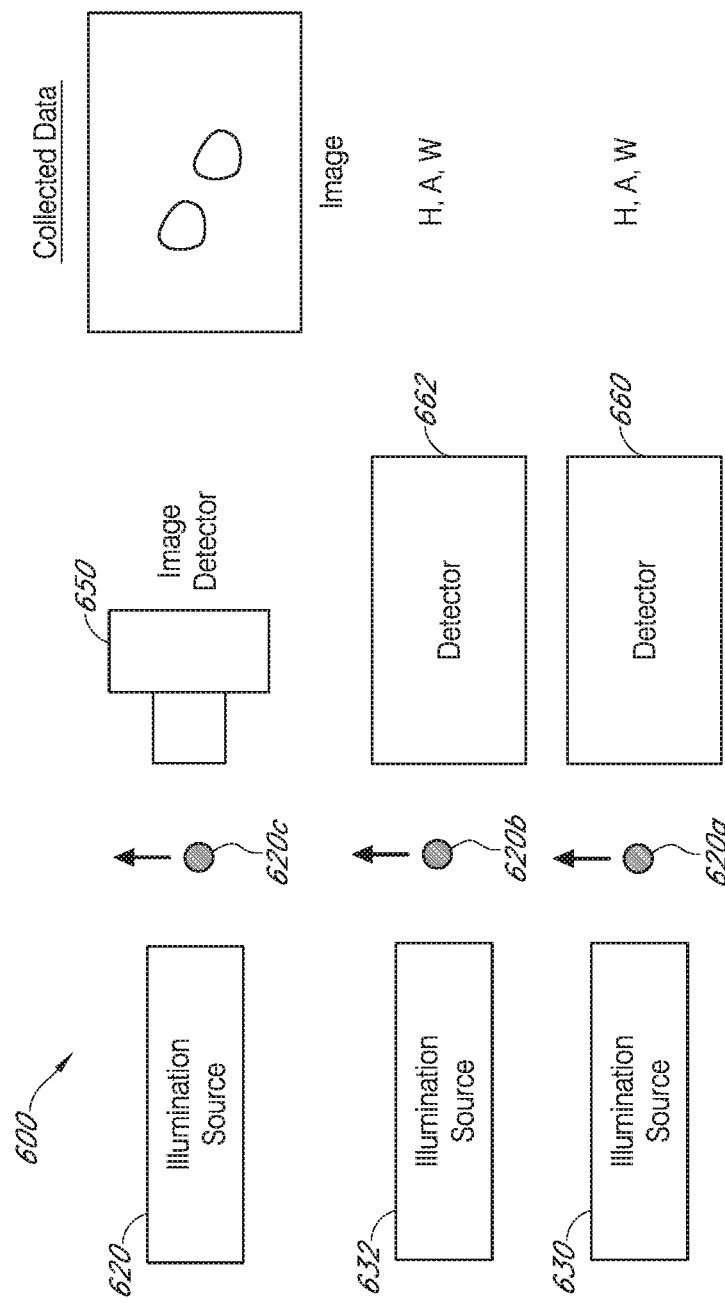
FIG. 6 depicts the collection of conventional flow cytometry data (height, area, and width) and also image data for each of several particles.

FIG. 6 provides system 600 having an exemplary configuration in which conventional flow data and image data is collected from a particle. As shown, a particle may transit from a first position 620a to a second position 620b and to a third position 620c, with the first position being subject to a first illumination source 630 and a first detector 660, the second position being subject to a second illumination source 632 and a second detector 662, and a third position subject to an illumination source 620 and an image detector 650. As described, conventional flow data consists of several parameters collected from the pulse of light collected by the detector. These parameters may include pulse height (H), pulse area (A), and pulse width (W). This configuration is beneficial regardless of whether there are velocity changes between interrogation zones.

With the addition of an image of the particle, a user can utilize these data in several different ways to determine if the data from a specific cell or particle was collected when another cell was present. For instance, by looking at the image, it is possible to assess coincidence for a given event providing a zeroeth order determination of data quality. In a more complex manner, the image can be processed to determine if a coincident event is present for any data point in the entire data set. In this case, the user can process the image data according to a specific set of rules to determine which events were collected during a coincident condition within a data set. The user can then discard the data associated with the coincident events to conserve data storage space or do additional analysis.

It is to be noted that coincidence is not always disadvantageous. There are instances where two cells in contact may represent a cell-cell interaction of interest. As spatial data is limited in conventional flow cytometers, the detection of such interactions is difficult. The addition of an imaging capability to a conventional flow cytometer allows a user to determine this condition by viewing or processing the image. This information can then be associated with the specific events within the conventional flow cytometry data that was collected.

Image-Based Sorting

Figure 7:
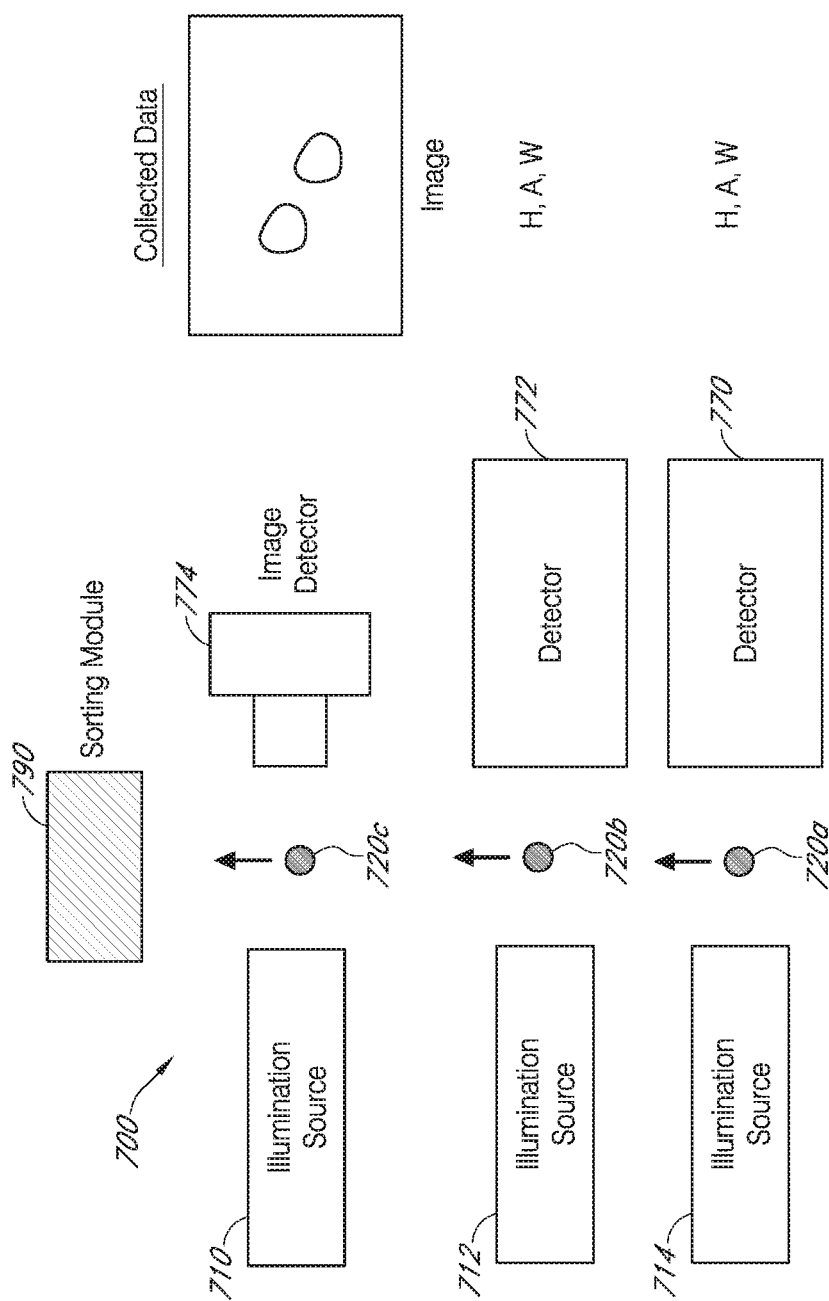
FIG. 7 depicts a flow cytometer that collects conventional flow cytometry data and captures image(s) of particles before they are sorted.

Flow cytometry sorting involves collecting traditional flow cytometry data (integrated signal) from individual cells to make a decision to sort a cell. It would be advantageous for a user to have a corresponding image of what has been sorted. By adding an imaging capability in-line with conventional flow cytometry detectors as shown in FIG. 7, images can be associated with the particle that has been sorted. The image will contain information not present in the conventional flow cytometry data such as cell morphology, nuclear size/shape, coincident interactions, and the like.

As shown by system 700 in illustrative FIG. 7, a particle may transit from a first position 720a to a second position 720b and to a third position 720c, with the first position being subject to a first illumination source 714 and a first detector 770, the second position being subject to a second illumination source 712 and a second detector module 772, and a third position subject to a third illumination source 710 and an image detector 774. As described, flow data may include several parameters collected from the pulse of light collected by the detector. These parameters may include pulse height (H), pulse area (A), and pulse width (W). This configuration is beneficial regardless of whether there are velocity changes between interrogation zones.

The system of FIG. 7 may further include a sorting module 790, which sorting module may act to sort particles on the basis of a presence, absence, or level of data that represents the presence, absence, or level of one or more specific markers, cellular functions, physical characteristics, and the like. Some exemplary sorting modules include mechanically-based sorters, e.g., catch tube sorters, valve sorters, and the like. Droplet sorters and bubble sorters are also suitable, as are field-based sorters such as electrical, acoustic, and magnetically-based field sorters. The magnitude of a field may be constant, but may also be adjusted or changed over time according to the user's needs.

A system that executes sorting decisions using conventional flow cytometry data and then capture images is advantageous to flow cytometry users. In some embodiments, one may within such a system use the sort trigger to trigger the camera such that only images of the sorted particles are saved. Within such a method, the user may draw gates to select any particle that has properties that fall within those gates. The negative is also possible where the user would like data that falls outside the selected gates. Data may be analyzed in real time to determine sorting and imaging decisions. By selectively gating for sorting and imaging, data storage space requirements can be greatly reduced. In addition, the processing burden to analyze the data is also greatly reduced.

Sorting Followed by Image or Other Analysis

The sorting process itself can be used as a tool for switching analysis regions if the action of sorting moves the particle or cell into, e.g., (i) a different flow channel, (ii) a different chamber, or (iii) a different part of the flow having a different speed. This technique can be particularly advantageous for rare cells where velocity can be greatly reduced or even stopped for the cell. A physical or field based cell trap can also be utilized to collect cells either in the imaging/analysis region or after such a region.

Figure 8:
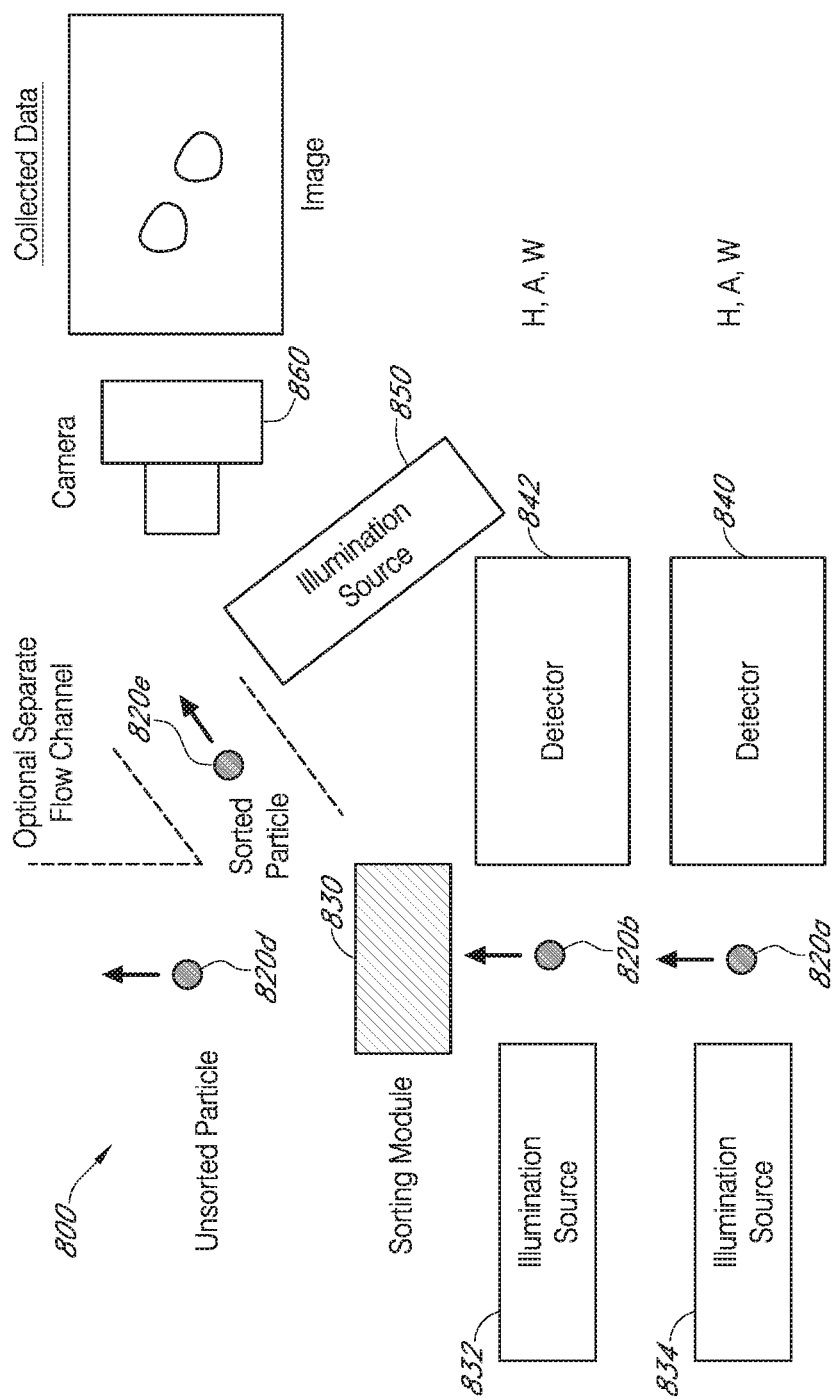
FIG. 8 depicts a flow cytometer that captures image(s) or other data of particles/cells after they are sorted; and where the post-sort region may further incorporate a trap and or other means for downstream manipulation of sorted particles/cells.

As shown by system 800 in FIG. 8, a particle may transit from a first position 820a (where the particle is subject to illumination from a first illumination source 834 and to a first detector 840), to a second position 820b, where the particle is subject to second illumination source 832 and a second detector 842. A sorting module 830 may then act to sort particles on a particular basis such that sorted particles (e.g., the particle shown at position 820e) are routed in one direction (e.g., continuing in the same flow channel) and unsorted particles or particles that did not meet the applicable sorting criteria (e.g., the particle at position 820d) are routed in another direction (e.g., being routed into a separate flow channel). An image detector 850 (e.g., a camera) may collect images of sorted particles.

A system may, of course, be configured to include multiple sorters, which multiple sorters may act to sort particles based on different particle characteristics. For example, a system may include a first sorter that acts to sort particles based on size and a second sorter that sorts particles based on the particles' electrical charge. A system may also include one or more imagers so as to allow for collection of particle images before or after a sorting stage.

In some embodiments, a channel may split from a "trunk" region into multiple "branch" regions. The flowrate may be slower in the trunk than in the branch regions, though this is not a requirement. Such an embodiment may be suited to applications where there is particle sorting (e.g., where cells are sorted by flow data and then cells of potential interest are imaged while the cells that are not of interest are directed down an alternative branch). In some embodiments, one or more branch regions may include its own illumination source and/or detector so as to allow for multiplexed analysis of a sample.

Imaging techniques that might otherwise be limited can then be employed to collect higher content information. Examples of such imaging techniques that can greatly benefit from employing the embodiments disclosed herein include time resolved imaging, 3D confocal imaging, and 3D holographic imaging. In such a device, collected cells can be further manipulated downstream to prepare them for other analysis by exchanging buffers/adding other reagents.

Overlapping, Composite Images and Color Images

Flow cytometrists operating conventional flow cytometers may run several different assays on the cells simultaneously. For instance, a researcher may be interested in CD4, CD8, and CD45 expression on the cell. This requires several detection channels to discern the contribution from each associated label. Likewise, when imaging a cell, it is of interest to have the ability to run several different labels that display where on the cell interactions occur.

Traditionally, the spatial discernment has been accomplished by creating several images at different wavelengths. For instance, methods exist to create multiple, separate images on imaging arrays or even on a single pixelated detector. Similarly, a flow cytometry imaging method has been proposed utilizing frequency multiplexing methods where wavelength-filtered light is collected on separate PMTs and later processed to create an image.

It may be advantageous to collect several pieces of information (e.g., scatter and fluorescence) from the same image, thereby reducing complexity, cost, and required storage space of the system. In one method, several signals containing different information can be simultaneously collected within the same image to create a composite image. For instance, there are many dyes that stain in spatially specific areas of the cell (e.g., nuclear stains) that can be used to create image contrast. By using appropriate filters, contrast can be created between different cellular structures.

Figure 9:
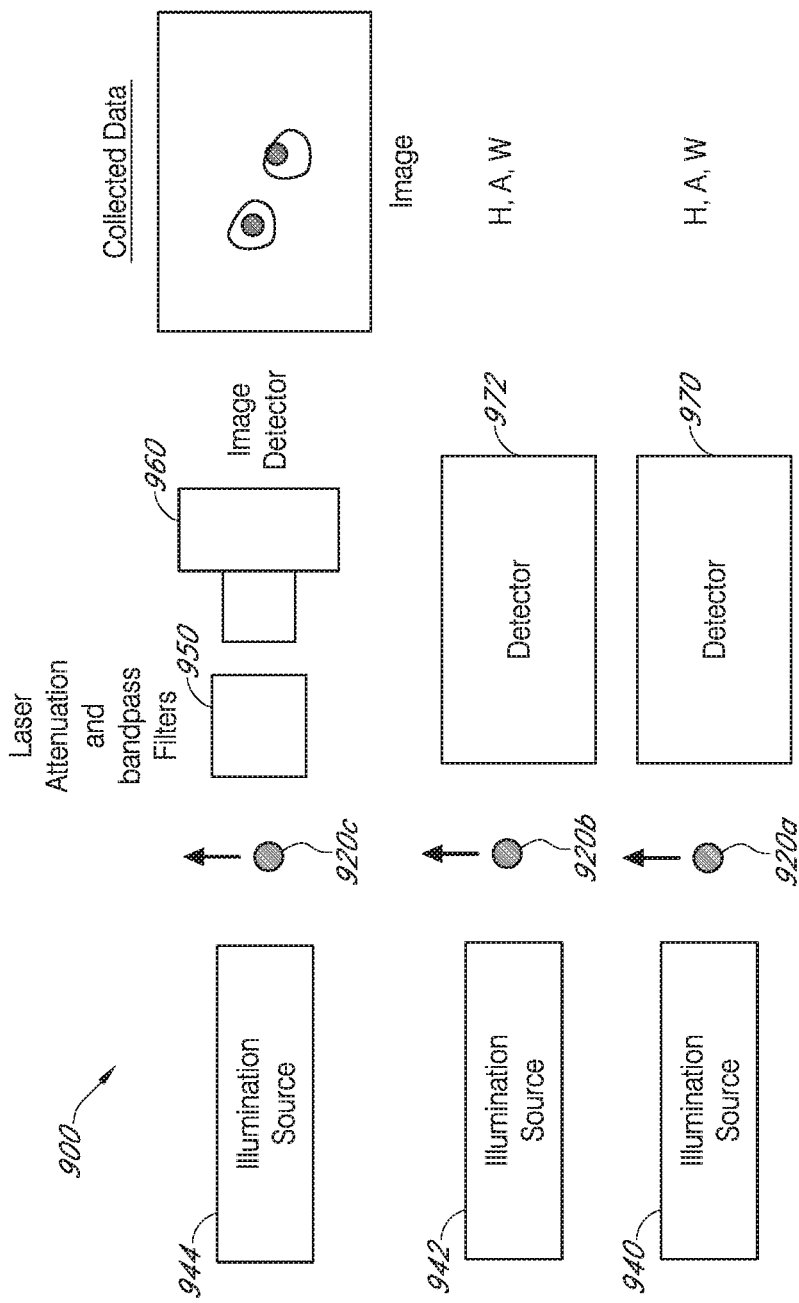
FIG. 9 depicts a system configured to capture composite images, such as collecting both bright field and fluorescence data within the same image.

FIG. 9 provides an exemplary system 900. As shown, a particle may transit from a first position 920a (subject to a first illumination source 940 and a first detector 970), to a second position 920b (subject to a second illumination source 942 and a second detector 972) to a third position 920c (where the particle may be subject to a third illumination source 944 and an image detector 960 (e.g., a camera as depicted in FIG. 9). One or more filters 950 (e.g., laser attenuation, bandpass) may be disposed so as to adjust the light received by the image detector 960.

As one example, a user might stain a nucleus with an appropriate dye and collect a bright field or dark field image. With the appropriate filters, additional contrast can be given to the nucleus. Filters in this situation may include a laser attenuation filter to reduce the scatter signal and a bandpass filter to isolate the nuclear stain from other fluorescent signals. To further increase contrast, one may illuminate the target with an illumination beam that is not parallel to the imaging axis, thereby also reducing the amount of light from the illumination source reaching the image sensor.

Measurements such as size, morphology, and granularity of the cell can also be determined from the composite image as well as nuclear size and position within the cell. With the advent of extremely bright dyes, e.g., polymer dyes that can be attached to specific antibodies, antibody-based dye conjugates may also be used to create contrast within the image.

In the above example and in various embodiments of the disclosed technology, there are various dyes and stains that can create specific contrast within the composite image. Stains can be included to illuminate compartments, structures, and cellular boundaries. In these cases, one may include several stains within a single image with the use of the appropriate filters. In addition, increased contrast can be created through the use of absorbing dyes to isolate and enhance contrast of specific spatial entities.

In a similar method, composite information can be collected with the use of color dyes. For instance, Trypan Blue can be used as a live/dead stain. With the use of a color camera or the appropriate set of filters as discussed above, the blue stain can be superimposed on top of the bright field or dark field image.

The use of monochromatic light sources such as lasers also creates absorption contrast for dyes based on absorption of specific dyes at the wavelength(s) used for excitation. Absorbance information of more than one excitation source can be resolved with filters or alternately with spatial or temporal separation of the excitation sources. It should also be noted that many fluorescent dyes have strong extinction coefficients that can add spatial contrast through absorbance. Further, techniques have been developed using targeted chemical moieties, e.g., click chemistry, that allow specific designed color staining of desired structures that are made to incorporate these chemical reaction sites.

The myriad of dyes and stains to label structures and volumes within the cells is large and there are many combinations that can be used to obtain useful information from composite or color images. Images can contain bright field, dark field, fluorescence, or color images, or any combinations of the foregoing.

Astigmatism Correction

Typical imaging methods in flow cytometry use a lens to collimate the light received from the object. This collimated light is then passed through a series of dichroic and bandpass filters before being imaged onto a detector. It is advantageous to directly image the object without the need to collimate the light for traversal through the light dispersing/conditioning filter elements. This is problematic as passing focused or converging light through tilted dichroic mirrors introduces asymmetries into the propagation path as a result of the tilted geometry. This results in aberrations such as astigmatism.

Figure 10:
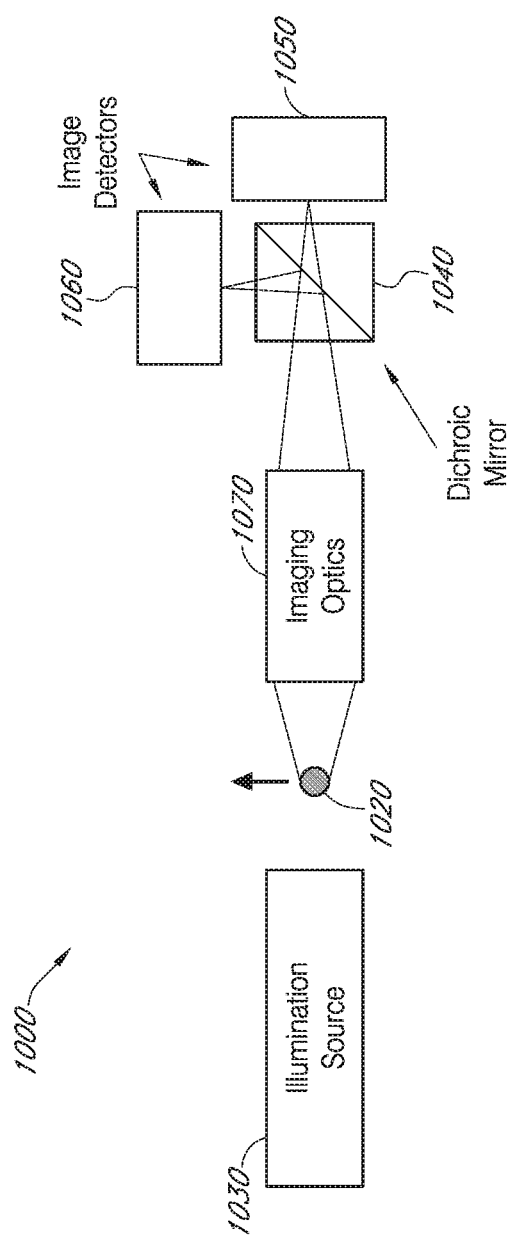
FIG. 10 depicts a converging waveform created by imaging optics; and also where a dichroic selectively allows light passage or reflection in a manner that creates aberration free images while using multiple cameras.

FIG. 10 provides a system 1000 configured to split light in two directions with use of a solid element having a dichroic coating as opposed to using a tilted dichroic mirror. As shown in the figure for system 1000, a particle at position 1020 is subject to illumination source 1030. Imaging optics 1070 and a dichroic mirror 1040 that does not introduce asymmetry in the propagation path (e.g., a dichroic coating within a solid element such as the cube depicted in FIG. 10) are configured to process light that is then collected by image detector 1050 and image detector 1060. Other solid element configurations for dichroic mirror 1040 are also possible, such as cuboid configurations that introduce little or no aberrations. Furthermore, as depicted in FIG. 10, imaging optics 1070 includes a converging element (e.g., a converging lens). In such a configuration, the converging waveform does not experience a spatial asymmetry in the propagation path. In this way, a nearly aberration-free image is produced in both propagation directions. In addition, with such arrangements, it is possible to create geometries where more than two image detectors can be used at separate locations and still facilitate the creation of quality images at different wavelengths that are free from aberrations.

In a similar manner, solid dichroic elements and/or transparent elements can be used to change the focal length of the converging beam. By inserting materials with different light propagation velocities into the light path, the focal distance can be changed along that path.

Figure 11:
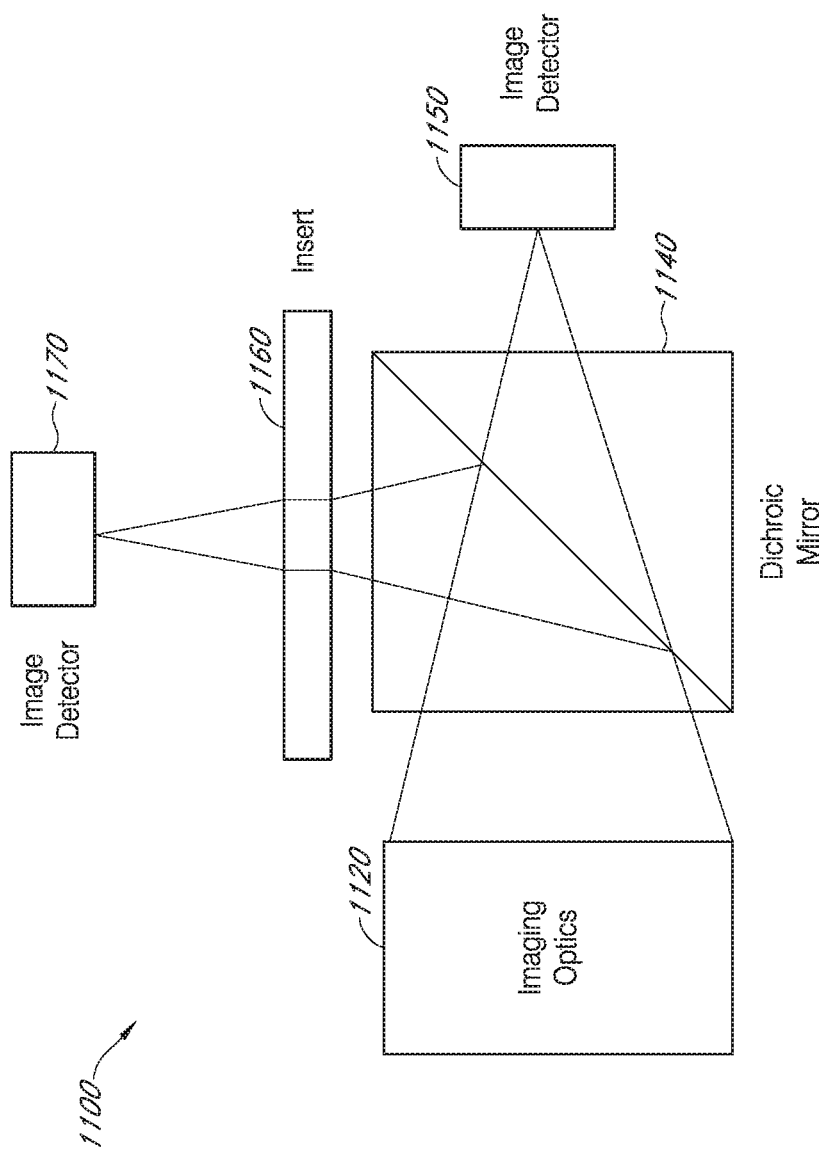
FIG. 11 provides an illustration of an embodiment in which insertion of a quartz plate extends the focus distance to one of the image detectors.

FIG. 11 provides a system 1100 configured to change the focal distance associated with one image detector within the system while employing a single focusing lens to create a converging waveform. As shown in FIG. 11, system 1100 may include a dichroic mirror 1140 (e.g., a dichroic cube as illustrated) that is optically connected with imaging optics 1120 and image detector 1150. As discussed previously with respect to FIG. 10, dichroic mirror 1140 is depicted as a cube but can possess other configurations such as a cuboid configuration. A further image detector 1170 is optically connected with the dichroic mirror 1140, with an insert 1160 (e.g., a quartz plate insert) present between the dichroic mirror 1140 and the image detector 1170 to increase the focal length. Without being bound to any particular theory, by inserting a solid material insert such as quartz into the propagation path, the focus length of the beam will increase flexibility for allowing configurations where equal optical path lengths to the image detectors may not be possible.

Extended Depth of Field

Depth of field is one of the more difficult effects to address in imaging flow cytometry. Due to the large magnifications required, depth of field is typically quite small. The small value of the depth of field requires the particle be placed with a high degree of accuracy in the object plane. In a flowing system this is a challenge, as particles must then be aligned with tolerances in the micron range to insure images from all the particles that flow by the sensor are in focus.

Figure 12:
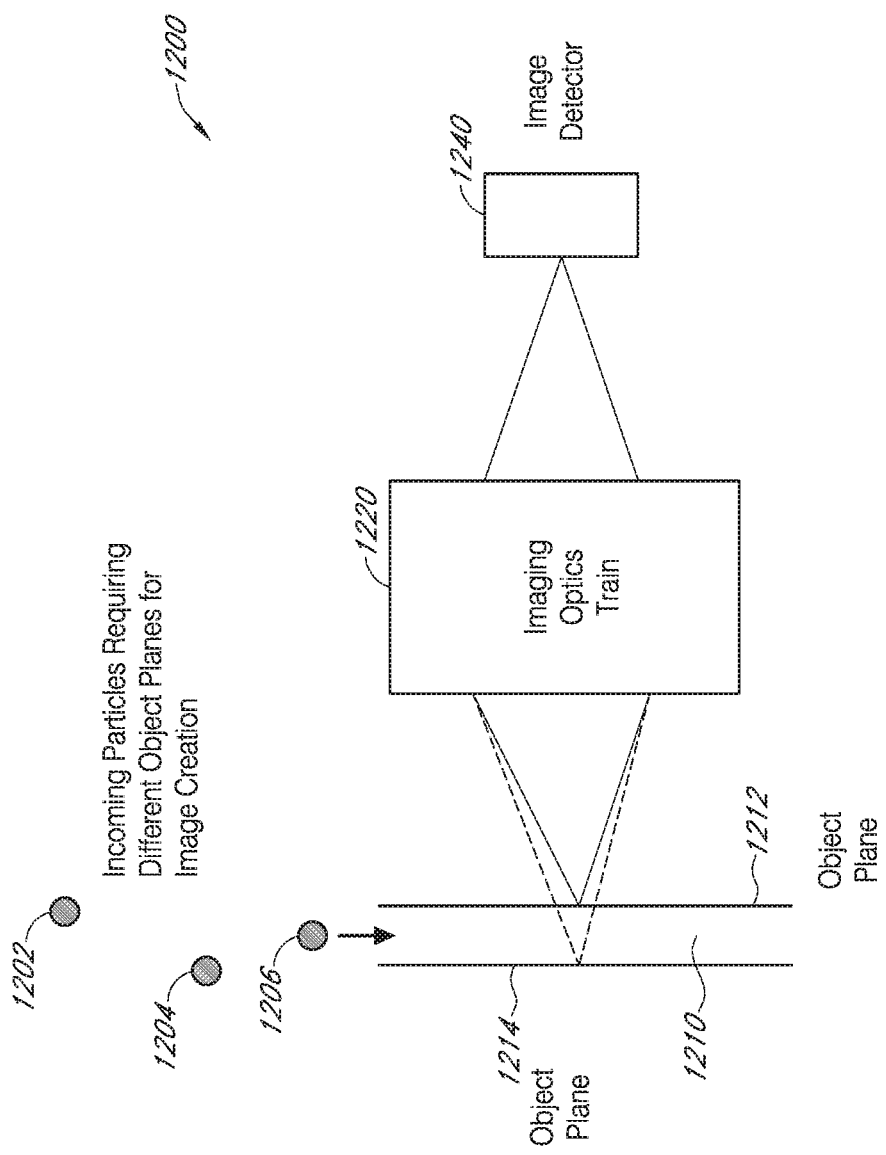
FIG. 12 provides an embodiment in which multiple object planes are used by the imaging optics for particles that slightly differ in trajectory past the imaging system; for imaging systems with a shallow depth of field, such an arrangement can reduce the requirement for highly accurate particle positioning and can also increase depth of field in conventional flow optics, expanding the range of useful high numerical aperture (NA) optical designs.

One method to address this issue is to create a system with multiple object planes. This can be done by moving the object plane during the image capture. By traversing the object plane the image will be in focus at some point during the sweep. The movement of the object plane can be accomplished by rapidly changing the characteristics of the imaging system. This can be done by moving an element within the optical train or by rapidly manipulating one of the optical elements to effectively change the position of the object plane. FIG. 12 shows an example of imaging with multiple image planes.

As shown in FIG. 12, during operation, system 1200 may include particles 1202, 1204, and 1206 entering flow channel 1210. Different object planes (e.g., a first object plane 1212 and a second object plane 1214) are also shown. An imaging optics train 1220 may operate so as to sweep and collect images at multiple object planes, which images are then collected by image detector 1240. The image plane may be moved by mechanical means, such as rapidly moving the imaging optics, or by using optical components that can rapidly change the focal distance of the system (e.g., varifocal lenses). Alternatively, multiple planes can be collected simultaneously using lens arrays. Furthermore, while FIG. 12 depicts a first object plane 1212 and a second object plane 1214, alternative embodiments may have more than two object planes (e.g., 3, 4, 5, and so on) based upon the configuration of a particular system, the desired performance capabilities, and compatibility with other aspects of system 1200 (e.g., the abilities of the imaging optics train 1220). System 1200 may additionally include other aspects not expressly depicted, such as one or more illumination sources, in accordance with the other embodiments disclosed herein.

This same method can also be used in conventional flow cytometry optics to extend depth of field, thereby increasing particle positioning tolerance and allowing for the use of higher magnification, high numerical aperture (NA) objectives that normally have a shallow depth of field.

Extended Depth of Field for Illumination

Similarly, the focus of the illumination light can be extended by rapidly sweeping the focal waist of the source. This technique can create more uniform illumination and potentially alter beam coherence, diminishing undesired effects such as speckle. The technique is useful for imaging, and it can also be applied to conventional flow cytometry, where uniform illumination is desirable for higher precision of quantitative fluorescence and scatter data. An example of such a technique is illustrated in FIG. 13.

Figure 13:
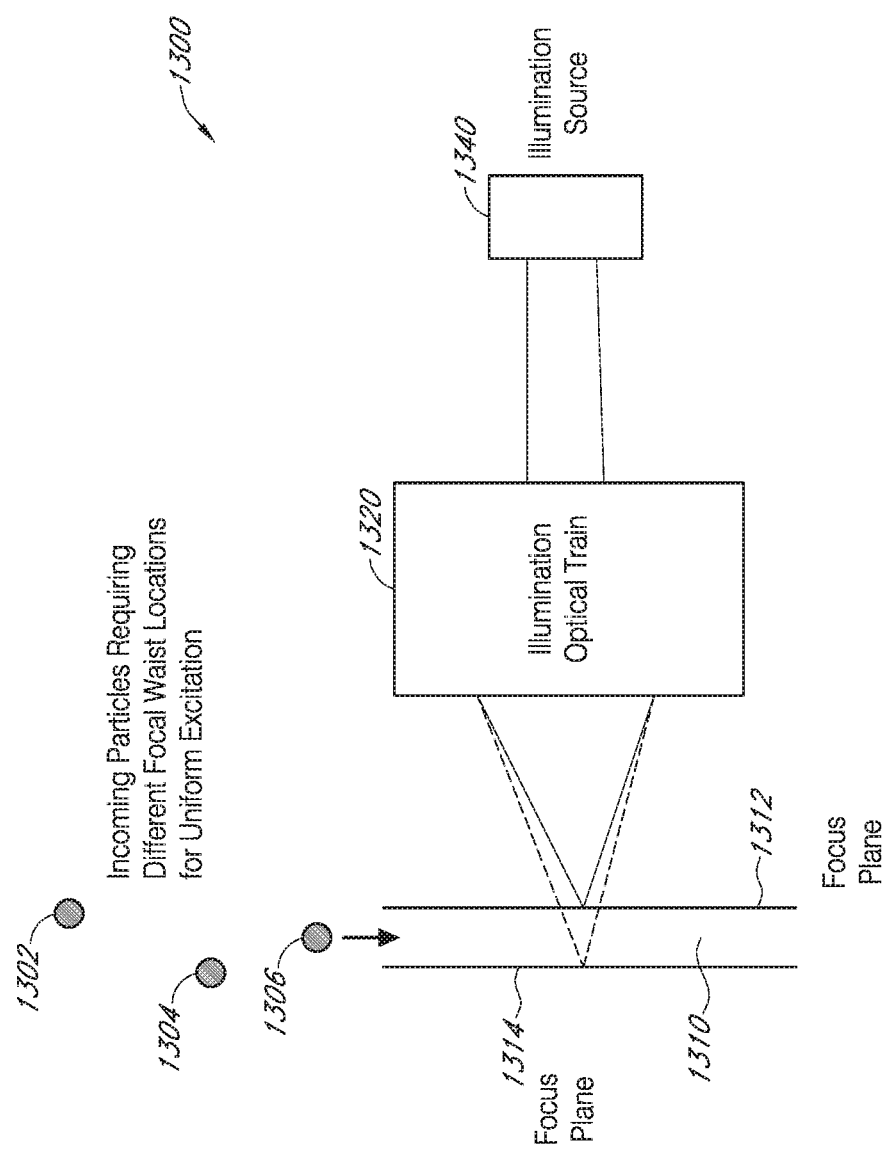
FIG. 13 provides an embodiment in which multiple focal planes used by the illumination optical train produce more uniform illumination over greater focal depth, thereby increasing image quality, reducing laser speckle, and decreasing sensitivity to object positioning.

As shown in FIG. 13, during operation, system 1300 may include particles 1302, 1304, and 1306 entering flow channel 1310 at different object planes (e.g., a first focus plane 1312 and a second focus plane 1314). An illumination optics train 1320 may operate so as to sweep and collect data at multiple focus planes, with illumination supplied by illumination source 1340. The focus plane may be moved by mechanical means, such as rapidly moving the imaging optics, or by using optical components that can rapidly change the focal distance of the system (e.g., varifocal lenses). Furthermore, while FIG. 13 depicts a first focus plane 1312 and a second focus plane 1314, alternative embodiments may have more than two focus planes (e.g., 3, 4, 5, and so on) based upon the configuration of a particular system, the desired performance capabilities, and compatibility with other aspects of system 1300 (e.g., the abilities of the illumination optical train 1320). System 1300 may additionally include other aspects not expressly depicted, such as one or more detectors (including one or more image detectors), in accordance with the other embodiments disclosed herein.

This same method can also be used in conventional flow cytometry optics to extend depth of field, thereby increasing particle positioning tolerance and allowing for the use of higher magnification, high NA objectives that normally have a shallow depth of field.

Non-Normal Illumination

In most imaging systems, the illumination light is parallel to the optical axis of the system. There are applications where greater contrast is needed, especially if the image does not offer much contrast to the surrounding medium. In such instances, microscopes may use structured illumination such as illuminating the sample with a cone of light to eliminate light that is parallel to the imaging axis. This may be done by using an axially symmetric cone of light for illumination.

Figure 14:
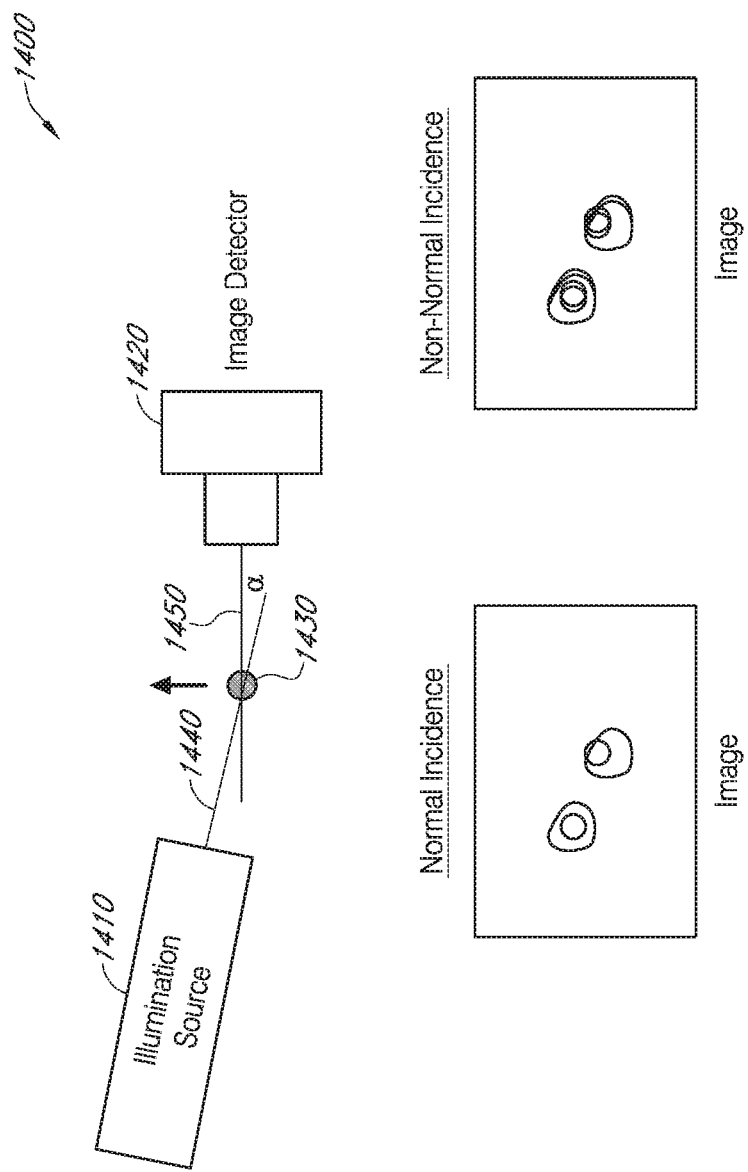
FIG. 14 provides an embodiment in which optical axes of illumination and imaging within the optical system are offset by an angle .alpha. to create shadow regions within the resulting images that provide enhanced contrast.

As shown in FIG. 14, during operation, system 1400 may include a particle 1430. System 1400 comprises an illumination source 1410 configured to illuminate particle 1430, and an image detector 1420 configured to collect a signal resulting from the illumination of particle 1430. By illuminating the particle 1430 with light that is not parallel with the optical axis of the imaging system (oblique incidence) and is not axially symmetric about that axis, it is possible to create shadow regions within the image and accordingly increase contrast for cellular/particle features in the image.

The shadow regions can yield higher contrast by limiting the amount of illumination in regions adjacent to features in images such as cellular structures. In addition, off-axis illumination also reduces the amount of illumination light reaching the image detector further increasing image contrast. The depth of the shadows can be controlled by the offset angle between the two axes.

FIG. 14 displays a configuration where an illumination axis 1440 is offset by an angle .alpha. from an imaging axis 1450. In addition, illumination can be steered such that the reverberating illumination present in the flow cell is guided away from other interrogation zones that may also be present, such as those interrogation zones designed to collect conventional flow cytometry data.

As discussed above, FIGS. 10-14 illustrate various optical componentry configurations according to the present disclosure. It should be understood that any of the component configurations shown in FIGS. 10-14 may be used with any of the flow system configurations shown in FIGS. 1-9.

Exemplary Images

The following results are illustrative only, and should not be understood as limiting the scope of the present specification.

As explained elsewhere herein, comparatively higher particle velocities are typically used to collect conventional flow data. One feature of such an approach is that the less time a particle spends in the interrogation zone, the lower the probability of two particles being interrogated simultaneously and thus leading to an erroneous result. To image a particle, however, lower velocities are advantageous to minimize the particle's motion. This is illustrated by FIG. 15 and FIG. 16.

Figure 15:
FIG. 15 provides an image taken of a red blood cell traveling at 4 m/s (the exposure time is 1 microsecond)—as shown, the image is blurred and it is difficult to discern the cell boundary.

FIG. 15 provides an image taken of a red blood cell traveling at 4 m/s, with an exposure time of 1 microsecond. As shown, the image is comparatively blurred and it is difficult to discern the cell boundary.

Figure 16:
FIG. 16 provides an image of red blood cells taken with the same set up as FIG. 15 at a velocity that is four times slower, 1 m/s—as shown, motion blur is reduced and the exterior boundary of the cells is readily distinguishable.

By comparison, FIG. 16 provides an image of red blood cells taken with the same set-up as FIG. 15, but with the cells traveling at a velocity that is four times slower (i.e., at 1 m/s) than the velocity of the cells shown in FIG. 15. As shown in FIG. 16, motion blur is reduced and the exterior boundary of the cells is more readily distinguishable, as compared to the cell of FIG. 15.

Figure 17:
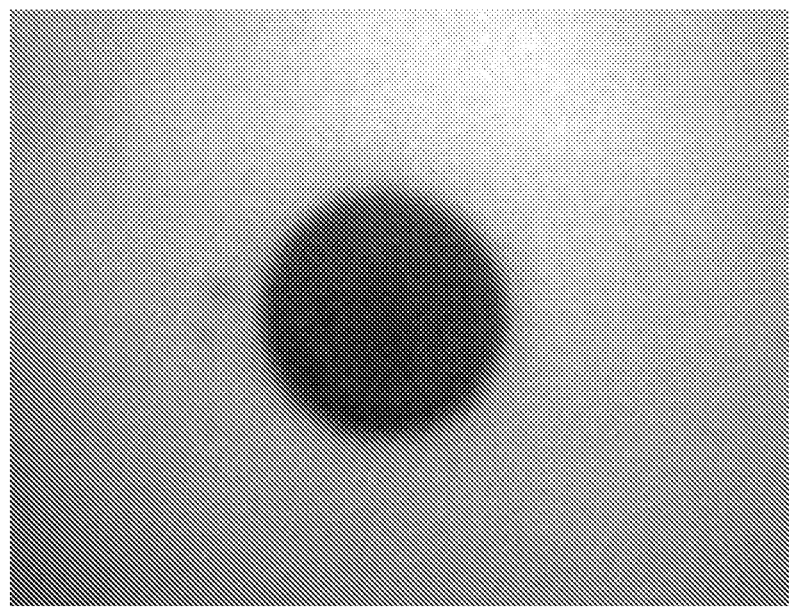
FIG. 17 provides an image of a bead traveling at about 1 m/s (bead is in focus)
Figure 18:
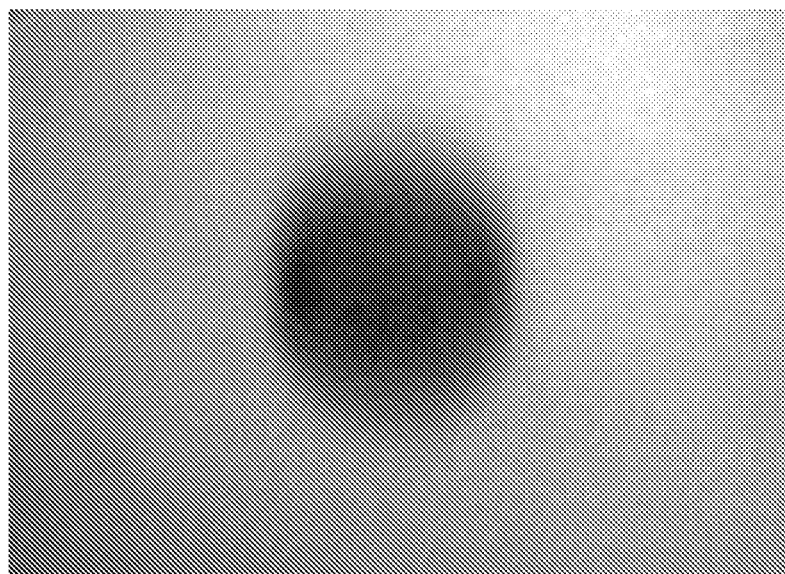
FIG. 18 provides an image of a bead traveling at about 8 m/s (bead is blurred).

FIG. 17 and FIG. 18 provide images of beads traveling at velocities of 1 m/s and 8 m/s (respectively). As shown, the image of the bead traveling at 1 m/s is in focus and is easily discernible. By contrast, the bead traveling at 8 m/s is blurred. The basic parameters of this test were (i) bead diameter: 15 microns; (ii) velocity 1 or 8 m/s; (iii) shutter time: 1 microsecond; (iv) lens magnification: 50.times.; (v) configuration: brightfield; (vi) illumination: LED; (viii) flow is left to right in the images.

In FIG. 17 and FIG. 18, at a velocity of about 1 m/s, the bead moved about 1 micron during the shutter cycle. At 8 m/s, the bead will move about 8 microns during the shutter. Because the bead was about 15 microns in diameter, the bead will thus move slightly more than one-half of its diameter during the shutter cycle. A system according to the present disclosure may be configured such that a particle moves less than 4 times its diameter during a shutter cycle, or less than 2 times its diameter during a shutter cycle, less than about 1 time its diameter during a shutter cycle, or even less than about 0.75 its diameter during a shutter cycle.

EXEMPLARY ASPECTS

The following aspects are illustrative only, and should not be understood as limiting the scope of the present specification or the appended claims.

Aspect 1. A system, comprising:

a flow channel, the flow channel having an inlet, and the flow channel defining a flow path for fluid communicated therethrough;

a first optical train comprising a first illumination source and a first detection module, the first detection module being disposed so as to receive a signal related to illumination of a first region of the flow channel by the first illumination source, the first region being located at a first distance from the inlet of the flow channel;

a second optical train comprising a second illumination source and a second detection module, the second detection module being disposed so as to receive a signal related to illumination of a second region of the flow channel by the second illumination source, the second region being located at a second distance from the inlet of the flow channel, the second distance being greater from the first distance, and (a) wherein the first region of the flow channel defines a first cross-sectional area, wherein the second region of the flow channel defines a second cross-sectional area, and wherein the first and second cross-sectional areas differ from one another in area, in shape, or in both area and shape, or (b) wherein (i) the system comprises a conduit entering the flow channel between the inlet of the flow channel and the first region of the flow channel, (ii) the system comprises a conduit entering the flow channel between the first region and the second region of the flow channel, or both (i) and (ii), or (c) wherein the system comprises a flowrate modulator configured to modulate a velocity in the flow path, or (d) the system further comprising a field module, the field module being configured to increase or reduce a field at a region of the flow channel so as to move at least some particles in a flow in the flow channel and sensitive to the field from a velocity streamline $S_0$ of particle velocity within the flow in the flow channel to a velocity streamline $S_1$ of particle velocity within the flow in the flow channel, wherein the particle velocity at $S_0$ during system operation differs from the particle velocity at $S_1$, between the first and second regions of the flow channel, or any combination of (a), (b), (c), or (d).

A flow channel may have a circular cross-section, but it may also be oblong, polygonal, or irregular in its cross-section. Rectangular or square cross-sections are considered especially suitable, but are not required. A channel may have a cross-sectional dimension (e.g., diameter) in the range of from about 50 micrometers to about 10,000 micrometers.

Suitable first illumination and detection modules are described elsewhere herein.

The first region of the system may be a region of the flow channel that is disposed between the first illumination source and first detection modules, e.g., a section of the flow channel within which a particle may be illuminated by the first illumination source and that illumination (or a signal related thereto, such as a fluorescence) may be detected by the first detection module.

Similarly, the second region of the system may be a region of the flow channel that is disposed between the second illumination source and second detection modules, e.g., a section of the flow channel within which a particle may be illuminated by the second illumination source and that illumination (or a signal related thereto, such as a fluorescence) may be detected by the second detection module.

The first and second regions are suitably disposed at different distances, as measured along the flow channel, from the inlet of the flow channel. The separation between the first and second regions may be, e.g., from about 100 micrometers to about 10 mm, though this is not a requirement.

In some embodiments, the second region may be described as downstream relative to the first region. In some embodiments, the first region may be described as downstream relative to the second region. As described elsewhere herein, a flow channel may branch from a trunk portion into two or more flow branches. Alternatively, a flow channel may converge from two or more branches to a trunk portion. The flowrate in a trunk portion may differ from the flowrate in a branch portion.

Aspect 2. The system of Aspect 1, wherein the first and second cross-sectional areas differ from one another and the ratio of the first cross-sectional area to the second cross-sectional area is from about 100:1 to about 1:100, excluding 1:1. As some non-limiting examples, the ratio of the first cross-sectional area to the second cross-sectional area may be from about 100:1 to about 1:100, or from about 98:1 to about 1:98, or from about 90:1 to about 1:90, or from about 80:1 to about 1:80, or from about 70:1 to about 1:70, or from about 60:1 to about 1:60, or from about 50:1 to about 1:50, or from about 40:1 to about 1:40, or from about 30:1 to about 1:30, or from about 20:1 to about 1:20, or from about 10:1 to about 1:10, or from about 8:1 to about 1:8, or from about 6:1 to about 1:6, or from about 5:1 to about 1:5, or from about 4:1 to about 1:4, or from about 3:1 to about 1:3, or from about 2:1 to about 1:2, or from about 1.8:1 to about 1:1.8, or from about 1.5:1 to about 1:1.5, or from about 1.3:1 to about 1:1.3, or from about 1.1:1 to about 1:1.1.

In this way, the system effects, during operation, different particle velocities at the first region and the second region. In one embodiment, a particle may pass through the first region at a velocity $v_1$, and then pass through the second region at a velocity $v_2$, where $v_2 < v_1$ on account of the cross-sectional area of the flow channel at the first region being larger than the cross-sectional area of the flow channel at the second region. The greater velocity may be from, e.g., 1.0001 times to about 1000 times the lower velocity, or from 1.001 times to about 100 times the lower velocity, or from 1.01 times to about 10 times the lower velocity, or from about 1.01 to about 5 times the lower velocity.

Aspect 3. The system of any of Aspects 1-2, wherein the flow channel defines a major axis. This may be, e.g., in a cylindrical flow channel, where the major axis is the central axis of the cylindrical channel.

Aspect 4. The system of Aspect 3, wherein at least one of the first and second illumination sources is configured to provide illumination essentially parallel to the major axis of the flow channel. In some embodiments, at least one of the first and second illumination sources is configured to provide illumination that is essentially perpendicular to the major axis of the flow channel. The illumination may, of course, be at an angle that is between parallel and perpendicular to the major axis of the flow channel. As but a few examples, the illumination may be from about 1 to about 89 degrees relative to the major axis of the flow channel, or from about 3 to about 86 degrees relative to the major axis of the flow channel, or from about 7 to about 81 degrees relative to the major axis of the flow channel, or from about 11 to about 77 degrees relative to the major axis of the flow channel, or from about 17 to about 70 degrees relative to the major axis of the flow channel, or from about 23 to about 65 degrees relative to the major axis of the flow channel, or from about 30 to about 58 degrees relative to the major axis of the flow channel, or from about 37 to about 50 degrees relative to the major axis of the flow channel, or from about 40 to about 44 degrees relative to the major axis of the flow channel Aspect 5. The system of any of Aspects 1-4, wherein the flow path is at least partially nonlinear. Such a flow path may be, e.g., curved, kinked, or even comprise a corner. (One such embodiment is shown in FIG. 5, which figure provides a flow channel 520 with a non-linear, kinked flow path.) A flow path may include a bend or kink that is less than 90 degrees, less than 80 degrees, less than 70 degrees, less than 60 degrees, less than 50 degrees, less than 40 degrees, less than 30 degrees, less than 20 degrees, or even less than 10 degrees.

A flow path may diverge from a single channel into multiple channels, and may also converge from multiple channels into fewer channels or even into a single channel.

Aspect 6. The system of any of Aspects 1-5, further comprising a particle separator in fluid communication with the flow channel.

Aspect 7. The system of Aspect 6, wherein the separator is configured to divert particles based upon particle size, particle shape, particle mass, a signal associated with one or more particles, or any combination thereof. Suitable such separators are known to those of ordinary skill in the art. Some exemplary separators include, e.g., single cell sorting, fluorescent-activated cell sorting, magnetic cell sorting, buoyancy activated cell sorting, and the like.

Aspect 8. The system of Aspect 7, wherein the separator is configured to divert particles within the flow channel based upon a signal associated with one or more particles. As one example, a separator may be configured to divert particles that exhibit fluorescence of at least a certain intensity at a particular wavelength or range of wavelengths.

Aspect 9. The system of any of Aspects 6-8, wherein the system is configured to collect one or more images of separated particles. For example, a system may have a device (e.g., a camera, CCD) configured to image particles that are diverted to an alternative flow channel or flow stream.

Aspect 10. The system of any of Aspects 1-9, wherein at least one of the first or second detection modules comprises a plurality of detectors.

Aspect 11. The system of any of Aspects 1-10, further comprising a light reflector, a light splitter, or both in optical communication with at least one detection module.

FIG. 11 provides an exemplary such system. As shown in FIG. 11, an exemplary system may include a dichroic mirror 1140 (having reflective and splitting characteristics) in optical communication with image detector 1150 and image detector 1170.

Aspect 12. The system of any of Aspects 1-11, wherein one or both of the first or second optical trains is configured to effect imaging at two or more planes within the flow channel.

Aspect 13. The system of Aspect 12, wherein one or both of the first or second optical trains is configured to collect an image at two or more focal planes.

Aspect 14. The system of any of Aspects 12-13, wherein one or both of the first or second optical trains is configured to focus illumination at two or more planes.

Aspect 15. The system of any of Aspects 1-12, wherein the first optical train is configured such that an illumination axis from the first illumination source is offset by an angle from the first detection module, wherein the second optical train is configured such that an illumination axis from the second illumination source is offset by an angle from the second detection module, or both. The offset angle may be, e.g., from about 1 to about 90 degrees, e.g., about 1, 5, 10, 15, 20, 25, 30, 35, 40, 45, 50, 55, 60, 65, 70, 75, 80, 85, or even about 90 degrees.

Aspect 16. The system of any of Aspects 1-15, wherein the first illumination source, the second illumination source, or both comprises a laser, a lamp, a light-emitting diode (LED), and the like.

Aspect 17. The system of any of Aspects 1-16, wherein the first detection module, the second detection module, or both comprises a photomultiplier tube (PMT), avalanche photodiode (APD), a camera, a silicon photomultiplier (SiPM), and the like.

Aspect 18. The system of any of Aspects 1-17, wherein the system is configured such that (a) operation of the second optical train, (b) operation of the separator, if present, or both (a) and (b), are related to a signal collected by the first optical train.

Aspect 19. The system of any of Aspects 1-18, wherein the field module comprises a source of magnetic field, an electric field, an acoustic field, or any combination thereof.

Aspect 20. A method, comprising:
flowing a population of particles through a flow channel;
with a first optical train, illuminating at least some of the population of particles at a first region of the flow channel and collecting a first signal or lack thereof related to said illuminating;
with a second optical train, illuminating at least some of the population of particles at a second region of the flow channel and collecting a second signal or lack thereof related to said illuminating,
a particle velocity at the first region of the flow channel differing from a particle velocity at the second region of the flow channel, and
the first signal differing from the second signal.

In some embodiments, the first and second signals differ in intensity, wavelength, or both. As one example, one signal may be a fluorescence signal related to the excitation of a dye, and another signal may be a visual image of a call gathered under visible light. As another example, one signal may be a fluorescence signal related to excitation of a first dye, and another signal may be a fluorescence signal related to excitation of a second, different dye.

In yet another example, a first detector may collect a signal related to the fluorescence of a first dye located in a region subject to illumination from a first illuminator. A second detector may detect the absence of photons related to fluorescence of a second dye located in a region subject to illumination from a second illuminator, which absence of photons may be considered a signal.

Aspect 21. The method of Aspect 20, wherein the cross-sectional area of the first region of the flow channel differs from the cross-sectional area of the second region of the flow channel in area, shape, or both.

Aspect 22. The method of any of Aspects 20-21, further comprising introducing or removing fluid from the flow channel at a location between the first and second regions of the flow channel.

Fluid may be introduced such that the ratio of the volumetric flow rate of fluid at the second region to the volumetric flow rate at the first region is, e.g., 1.0001:1 to about 5:1, 10:1, 20:1, or even about 40:1. Fluid may be withdrawn such that the ratio of the volumetric flow rate of fluid at the second region to the volumetric flow rate at the first region is, e.g., 1:1.0001 to about 1:5, 1:10, 1:20, or even about 1:40.

The interrogation time for particles at the first and second regions may vary, and may be from about 0.1 microsecond to, e.g., one millisecond or even tens of milliseconds. As one example, a laser interrogation to collect a fluorescence signal from a particle may have an interrogation time in the range of one microsecond to tens of microseconds. A visible light interrogation to collect a standard image of a particle may have an interrogation time in the range of one millisecond to tens of milliseconds. The ratio of the particle interrogation time in the first region to the particle interrogation time in the second region may be in the range of from about, e.g., 1:100,000 to about 100,000:1 (e.g., 10,000:1 to 1:10,000) and all intermediate values Aspect 23. The method of any of Aspects 20-22, wherein the flow channel defines a major axis.

Aspect 24. The method of Aspect 23, wherein illuminating at least some of the population of particles at the first region of the flow channel, wherein illuminating at least some of the population of particles at the second region of the flow channel, or both, is effected by illumination essentially parallel to the major axis.

Aspect 25. The method of any of Aspects 20-24, wherein the flow channel defines a flow path that is at least partially nonlinear.

Aspect 26. The method of any of Aspects 20-25, further comprising separating at least some of the population of particles on the basis of the first signal, the second signal, or both.

Aspect 27. The method of any of Aspects 20-26, further comprising collecting an image of one or more separated particles. It should be understood that this may comprise collecting one or more images of particles that satisfied the separation criteria or that did not satisfy the separation criteria.

Aspect 28. The method of any of Aspects 20-27, further comprising directing illumination from the first optical train with an illumination reflector, an illumination splitter, or both.

Aspect 29. The method of any of Aspects 20-28, further comprising directing illumination from the second optical train with an illumination reflector, an illumination splitter, or both.

Aspect 30. The method of any of Aspects 20-29, further comprising operating the first optical train, the second optical train, or both so as to collect a signal at two or more planes within the flow channel.

Aspect 31. The method of any of Aspects 20-30, further comprising operating the first optical train, the second optical train, or both, so as to focus illumination at two or more planes within the flow channel.

Aspect 32. The method of any of Aspects 20-31, wherein the illumination axis from an illumination source of the first optical train is offset by an angle from a detection module of the first optical train, wherein illumination from a illumination source of the second optical train is offset by an angle from a detection module of the second optical train, or both.

Aspect 33. The method of any of Aspects 20-32, wherein the first signal, the second signal, or both is a fluorescence signal, a fluorescence image, a luminescence image, a phase contrast image, a holographic image, a bright field image, a dark field image, a scatter signal, or any combination thereof.

Aspect 34. The method of any of Aspects 20-33, wherein operation of the second optical train is related to the first signal collected by the first optical train. As one example, the second optical train may not operate to illuminate or detect unless a certain threshold signal (e.g., a certain level of fluorescence) is collected by the first optical train. In this way, the second optical train may operate to only gather information concerning cells or other particles that have satisfied one or more criteria that are gathered by the first optical train.

Aspect 35. The method of any of Aspects 20-34, further comprising correlating the first signal, the second signal, or both, to one of more characteristics of at least one of the population of particles. As one example, one may correlate the presence of a particular dye to the live/dead status of a cell, as described elsewhere herein. One may also, e.g., correlated the intensity of a signal (e.g., fluorescence) to a level of a marker or other dye in a cell.

Aspect 36. The method of any of Aspects 20-35, wherein the population of particles are flowing at a first fluid flowrate at the first region and a second fluid flowrate at the second region, and wherein the ratio of the first fluid flowrate to the second fluid flowrate is from about 40:1 to about 1:40, excluding 1:1.

Exemplary particle velocities (in the first or a second region) may be, e.g., in the range of centimeters/second to tens of meters/second, e.g., from about 0.1 m/s to about 10 m/s, from about 0.5 to about 5 m/s, from about 1 to about 2.5 m/s, or even at about 1.5 m/s.

Also without being bound to any particular theory, the disclosed systems may operate at volumetric flow rates of, e.g., from about 10 μl/min (microliters/minute) to about 1000 μl per minute. Flowrates of from about 10 to about 1000 μl/min, or from about 50 to about 700 μl/min, or from about 100 to about 500 μl/min, or from about 200 to about 400 μl/min are all considered suitable.

A system according to the present disclosure may operate at a rate of, e.g., from about 10 to about 100,000 cells/second. Rates of from about 10 to about 100,000 cells/second, or from about 50 to about 50,000 cells/second, or from about 100 to about 10,000 cells/second, or even from about 500 to about 5,000 cells/second are all considered suitable.

It should also be understood that a system according to the present disclosure may operate at rates of from about 10 to about 100,000 events/second. Rates of from about 10 to about 100,000 events/second, or from about 50 to about 50,000 events/second, or from about 100 to about 10,000 events/second, or even from about 500 to about 5,000 events/second are all considered suitable. By application of sorting and/or gating, a system may be configured to exclude certain cells/particles in a sample and analyze only non-excluded cells/particles so as to utilize system resources on only a subpopulation of the sample. As but one example, if a system is capable of operating at 50,000 events per second, the system would require 10 seconds to analyze a population of 500,000 cells. But if the system is configured to exclude 50% of the cells in the sample, the system could analyze the 250.000 cells of interest in only 5 seconds.

Aspect 37. A method, comprising:
communicating a population of particles through a flow channel, in a direction from a first region of the flow channel toward a second region of the flow channel;
with a first optical train, illuminating at least some of the population of particles at the first region of the flow channel and collecting a first signal related to said illuminating;
with a second optical train, illuminating at least some of the population of particles at the second region of the flow channel and collecting a second signal related to said illuminating,
increasing or reducing a field on a subset of the particles between the first and second regions of the flow channel,
the field being increased or reduced so as to move the subset of particles from a velocity streamline $S_0$ of particle velocity within the flow channel to a velocity streamline $S_1$ of particle velocity within the flow channel, wherein the particle velocity at $S_0$ differs from the particle velocity at $S_1$.

Without being bound to any particular theory, this may be performed so as to move particles (that are subject to the field) from a first velocity streamline at the center of a flow channel to a second velocity streamline at the wall of the flow channel, where the flow—according to standard Poiseuille law flow—at the wall is relatively slower compared to the flow at the center of the flow channel. In this way, the particles, when moved closer to the flow channel wall, may transit the second region at a lower velocity than the velocity the particles had when transiting the first region.

Aspect 38. The method of Aspect 37, wherein the field comprises a magnetic field, an electric field, an acoustic field, a gravitation field, a dielectric field, or any combination thereof.

Aspect 39. The method of any of Aspects 37-38, further comprising coupling the subset of particles to an entity sensitive to the field. Example entities include, e.g., magnetic particles, particles with different dielectric properties, particles with different densities, and particles with different compressibilities.

Aspect 40. The method of Aspect 39, wherein the entity comprises magnetic particles.

Aspect 41. The method of Aspect 39, wherein the entity comprises dielectric particles.

Aspect 42. A method, comprising flowing a population of particles through a system according to any of Aspects 1-19.

Aspect 43. A method, comprising operating a system according to any of Aspects 1-19.

What is claimed:
1. A system, comprising:
a flow channel,
the flow channel having an inlet, and
the flow channel defining a flow path for fluid communicated therethrough;
a first optical train comprising a first illumination source and a first detection module,
the first detection module being disposed so as to receive a signal related to illumination of a first region of the flow channel by the first illumination source, the first region being located at a first distance from the inlet of the flow channel;
a second optical train comprising a second illumination source and a second detection module,
the second detection module being disposed so as to receive a signal related to illumination of (i) a second region of the flow channel or of (ii) a region of a second flow channel by the second illumination source,
the second region of the flow channel or the region of the second flow channel being located at a second distance from the inlet of the flow channel,
the second distance being greater from the first distance, and
(a) wherein the first region of the flow channel defines a first cross-sectional area, wherein the second region of the flow channel defines a second cross-sectional area, and wherein the first and second cross-sectional areas differ from one another in area, in shape, or in both area and shape, and
(b) wherein (i) the system comprises a conduit entering the flow channel between the inlet of the flow channel and the first region of the flow channel, (ii) the system comprises a conduit entering the flow channel between the first region and the second region of the flow channel, or both (i) and (ii).

2. The system of claim 1, wherein the first and second cross-sectional areas differ from one another in area and the ratio of the first cross-sectional area to the second cross-sectional area is from about 100:1 to about 1:100, excluding 1:1.

3. The system of claim 2, wherein the first and second cross-sectional areas differ from one another in area and the ratio of the first cross-sectional area to the second cross-sectional area is from about 20:1 to about 1:20, excluding 1:1.

4. The system of claim 1, wherein the flow channel defines a major axis.

5. The system of claim 4, wherein at least one of the first and second illumination sources is configured to provide illumination essentially parallel to the major axis of the flow channel.

6. The system of claim 1, wherein the flow path is at least partially nonlinear.

7. The system of claim 1, further comprising a particle separator in fluid communication with the flow channel.

8. The system of claim 7, wherein the separator is configured to divert particles based upon particle size, particle shape, particle mass, a signal associated with one or more particles, or any combination thereof.

9. The system of claim 8, wherein the separator is configured to divert particles within the flow channel based upon the signal associated with one or more particles.

10. The system of claim 7, wherein the system is configured to collect one or more images of separated particles.

11. The system of claim 7, wherein the system is configured such that (a) operation of the second optical train, (b) operation of the particle separator, or both (a) and (b), are related to a signal collected by the first optical train.

12. The system of claim 1, wherein at least one of the first or second detection modules comprises a plurality of detectors.

13. The system of claim 1, further comprising a light reflector, a light splitter, or both in optical communication with at least one detection module.

14. The system of claim 1, wherein one or both of the first or second optical trains is configured to effect imaging at two or more planes within the flow channel.

15. The system of claim 14, wherein one or both of the first or second optical trains is configured to collect an image at two or more focal planes.

16. The system of claim 14, wherein at least one of the first or second optical trains is configured to focus illumination at two or more planes.

17. The system of claim 1, wherein the first optical train is configured such that an illumination axis from the first illumination source is offset by an angle from the first detection module, wherein the second optical train is configured such that an illumination axis from the second illumination source is offset by an angle from the second detection module, or both.

18. The system of claim 1, wherein the first illumination source, the second illumination source, or both comprises a laser, a lamp, a light-emitting diode, or any combination thereof.

* * * * *